(12) United States Patent
Bornens et al.

(10) Patent No.: US 7,955,838 B2
(45) Date of Patent: Jun. 7, 2011

(54) METHODS AND DEVICE FOR ADHESIVE CONTROL OF INTERNAL CELL ORGANISATION

(75) Inventors: Michel Bornens, Sceaux (FR); Manuel Thery, Paris (FR); Matthieu Piel, Bourron Marlotte (FR)

(73) Assignees: Institut Curie, Paris (FR); Centre National de la Recherche Scientifque, Paris (FR)

( * ) Notice: Subject to any disclaimer, the term of this patent is extended or adjusted under 35 U.S.C. 154(b) by 1354 days.

(21) Appl. No.: 10/572,101

(22) PCT Filed: Sep. 10, 2004

(86) PCT No.: PCT/IB2004/003091
§ 371 (c)(1),
(2), (4) Date: Mar. 10, 2006

(87) PCT Pub. No.: WO2005/026313
PCT Pub. Date: Mar. 24, 2005

(65) Prior Publication Data
US 2007/0042483 A1 Feb. 22, 2007

(30) Foreign Application Priority Data
Sep. 12, 2003 (EP) .................................... 03292259

(51) Int. Cl.
*C12M 1/34* (2006.01)
*C12M 3/00* (2006.01)

(52) U.S. Cl. .................. 435/287.9; 435/288.4; 422/547; 422/551; 422/552

(58) Field of Classification Search ................. 435/287.9
See application file for complete search history.

(56) References Cited

U.S. PATENT DOCUMENTS

| 5,108,926 A | 4/1992 | Klebe |
| 5,470,739 A | 11/1995 | Akaike et al. |
| 6,368,838 B1 * | 4/2002 | Singhvi et al. ................ 435/177 |
| 6,653,089 B2 | 11/2003 | Takayama et al. |
| 6,893,850 B2 | 5/2005 | Ostuni et al. |
| 7,288,394 B2 | 10/2007 | Ostuni et al. |

FOREIGN PATENT DOCUMENTS

| WO | WO 97/07429 | 2/1997 |
| WO | WO 01/70389 | 9/2001 |
| WO | WO 02/22787 | 3/2002 |

(Continued)

OTHER PUBLICATIONS

Gopalan, S. et al. "Anisotropic Stretch-Induced Hypertrophy in Neonatal Ventricular Myocytes Micropatterned on Deformable Elastomers" Dec. 23, 2002. Biotechnology and Bioengineering, vol. 81, Issue 5 pp. 578-587.*

(Continued)

*Primary Examiner* — William H Beisner
*Assistant Examiner* — Danielle Henkel
(74) *Attorney, Agent, or Firm* — Saliwanchik, Lloyd & Eisenschenk

(57) ABSTRACT

The present invention relates to methods and devices for adhering cells in a specific and predetermined position with an adhesive control of internal cell organization, methods for preparing such devices, methods for studying modifications of cell shape and global internal cell organization such as the distribution of cellular compartments, centrosome centering, spindle orientation, internal compartmentalization and internal transports, methods for screening compounds of interest which enhance or inhibit specific cell functions.

39 Claims, 17 Drawing Sheets

FOREIGN PATENT DOCUMENTS

Figure 1A:

| | | |
|---|---|---|
| WO | WO 02/086452 | 10/2002 |
| WO | WO 03/080791 A2 | 10/2003 |
| WO | WO 2004/069988 A1 | 8/2004 |

OTHER PUBLICATIONS

Teixeira, A. et al. "Epithelial contact guidance on well-definied micro- and nanostructured substrates" May 2003. Journal of Cell Science, vol. 116, pp. 1881-1892.*

Itoga, K. et al. "Cell micropatterning using phoopolymerization with a liquid crystal device commercial projector" Nov. 2003. Biomaterials 25, pp. 2047-2053.*

Marek, L. F. et al. "Organization of the Cytoskeleton in Square Fibroblasts", *Cell Motility*, 1982, pp. 115-130, vol. 2, No. 2.

Grzybowski, B. A. et al. "Generation of Micrometer-Sized Patterns for Microanalytical Applications Using a Laser Direct-Write Method and Microcontact Printing", *Analytical Chemistry*, Nov. 15, 1998, pp. 4645-4652, vol. 70, No. 22.

Branch, D. W. et al. "Long-Term Stability of Grafted Polyethylene Glycol Surfaces for use with Microstamped Substrates in Neuronal Cell Culture", *Biomaterials*, May 2001, pp. 1035-1047, vol. 22, No. 10.

Branch, D. W. et al. "Microstamp Patterns of Biomolecules for High-Resolution Neural Networks", *Medical and Biological Engineering and Computing*, 1998, pp. 135-141, vol. 36, No. 1.

Kam, L. et al. "Correlation of Astroglial Cell Function on Micro-Patterned Surfaces with Specific Geometric Parameters", *Biomaterials*, 1999, pp. 2343-2350, vol. 20, No. 23-24.

Brock, A. et al. "Geometric Determinants of Directional Cell Motility Revealed using Microcontacting Printing", *Langmuir*, 2003, pp. 1611-1617, vol. 19.

Craighead, H. G. et al. "Chemical and topographical patterning for directed cell attachment", *Current Opinion in Solid State and Materials Science*, 2001, pp. 177-184, vol. 5.

Kane, R. S. et al. "Patterning proteins and cells using soft lithography", *Biomaterials*, 1999, pp. 2363-2376, vol. 20.

Lom, B. et al. "A versatile technique for patterning biomolecules onto glass coverslips", *Journal of Neuroscience Methods*, 1993, pp. 385-397, vol. 50.

Nelson, C. M. et al. "Cell-cell signaling by direct contact increases cell proliferation via a PI3K-dependent signal", *FEBS Letters*, 2002, pp. 238-242, vol. 514.

Whitesides, G. M. et al. "Soft Lithography in Biology and Biochemistry", *Annu. Rev. Biomed. Eng.*, 2001, pp. 335-373, vol. 3.

Zhang, S. et al. "Biological surface engineering: a simple system for cell pattern formation", *Biomaterials*, 1999, pp. 1213-1220, vol. 20.

Parker, K. K. et al. "Directional control of lamellipodia extension by constraining cell shape and orienting cell tractional forces", *FASEB J.*, 2002, pp. 1195-1204, vol. 16.

Clark, P. "Cell guidance by micropatterned adhesiveness in vitro", *Journal of Cell Science*, 1992, pp. 287-292, vol. 103.

Nishizawa, M. et al. "Micropatterned HeLa Cell Culture on PEG Monolayer-Coated Glass Substrates", *Chemistry Letters*, 2002, pp. 904-905.

* cited by examiner

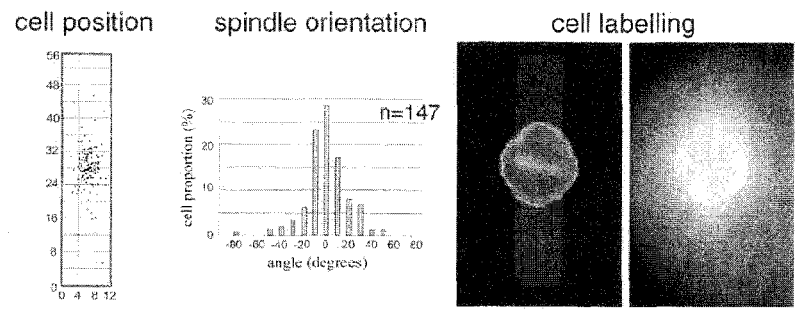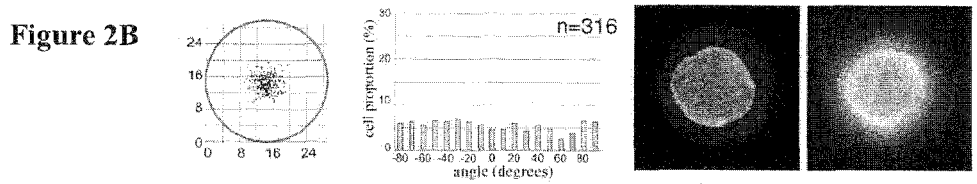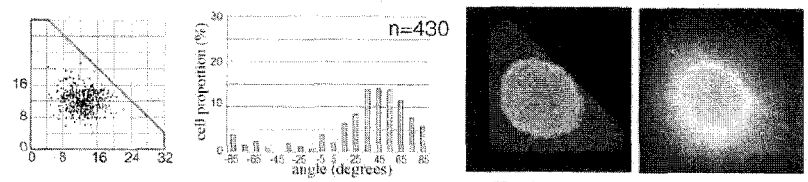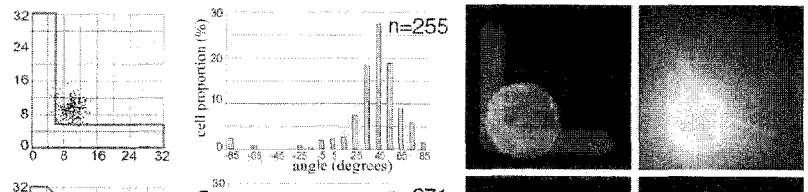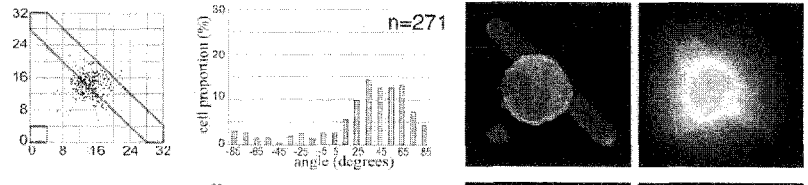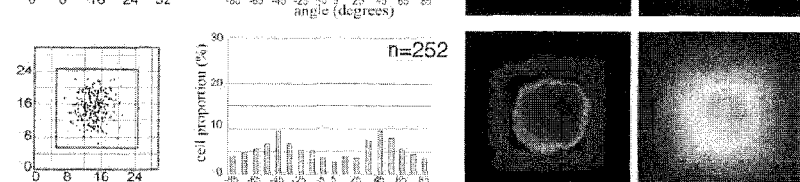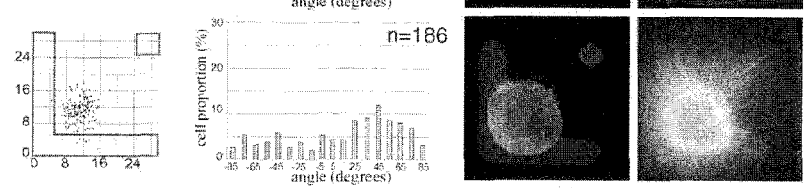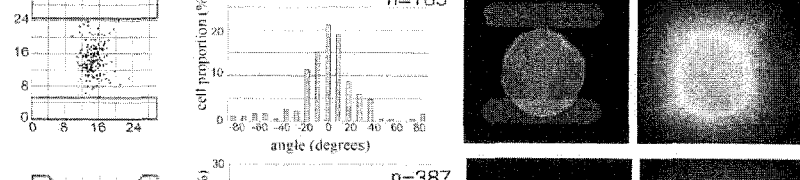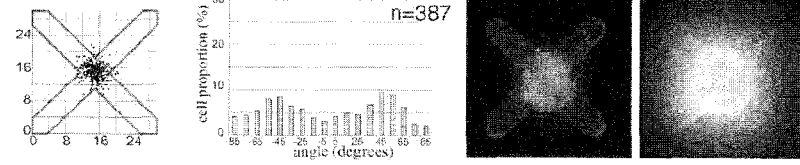

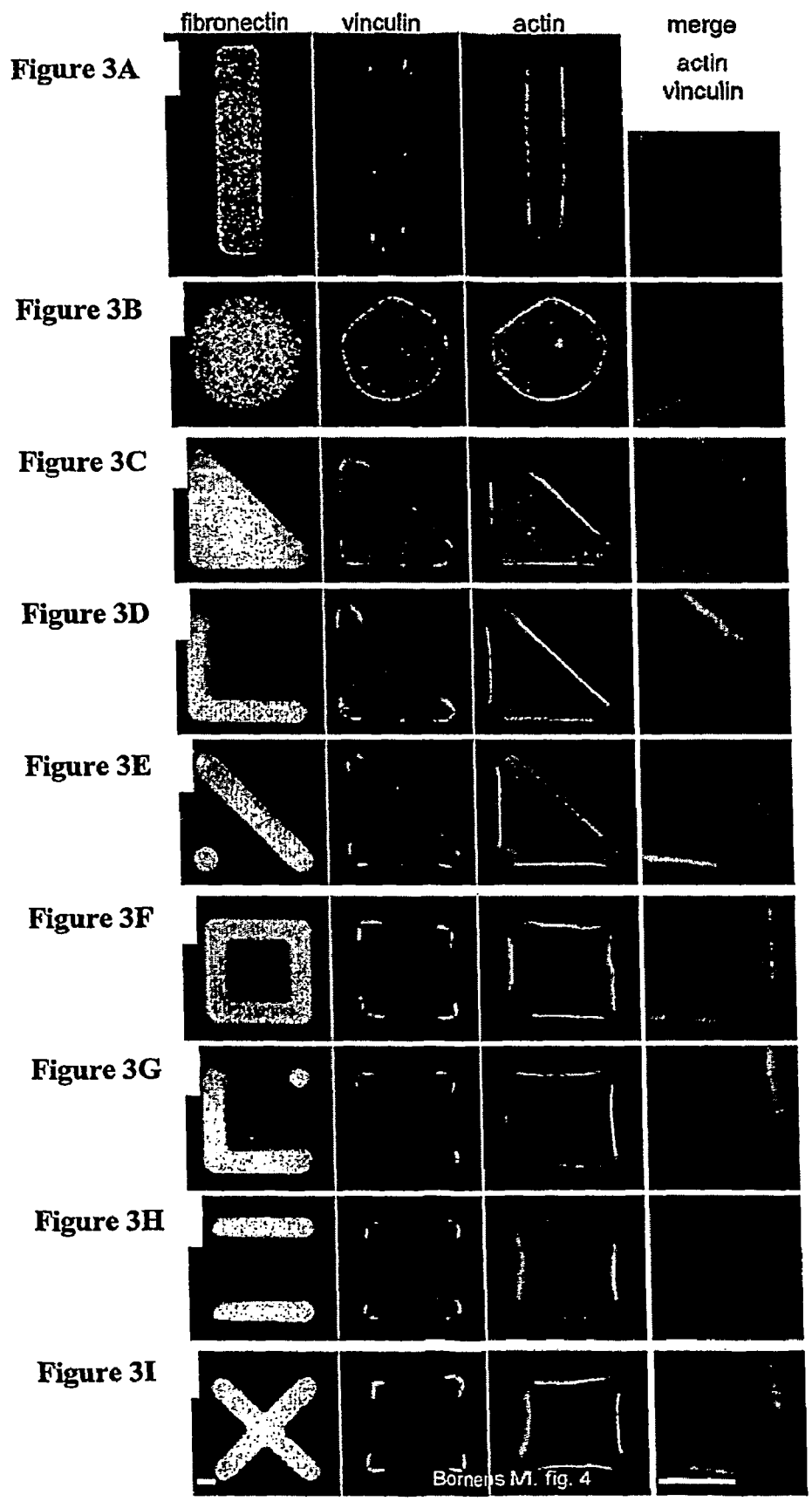

Figure 4A
Figure 4B
Figure 4E
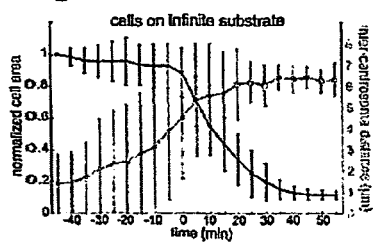
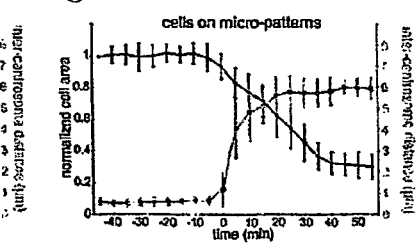
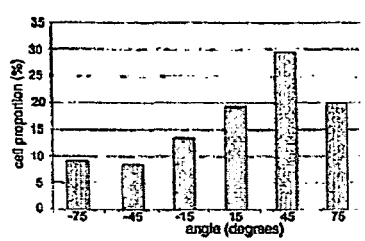
Figure 4C
Figure 4D

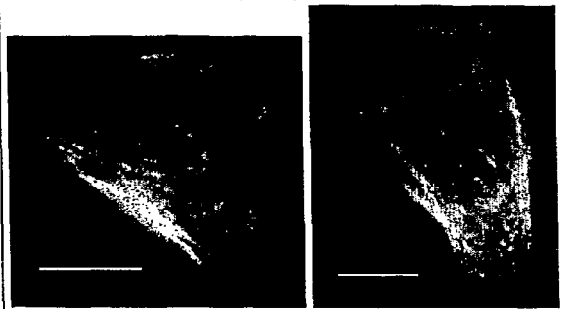
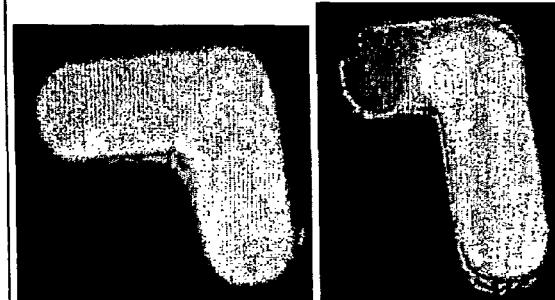

FIGURE 7A  VINCULIN
 
FIGURE 7B
FIGURE 7C  ACTIN
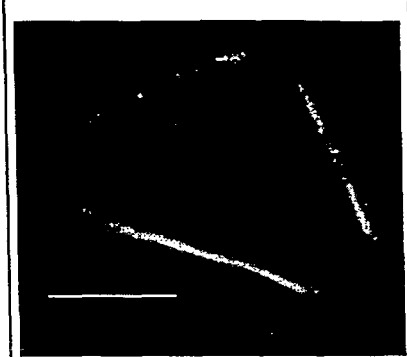 
FIGURE 7D
FIGURE 7E  FIBRONECTIN
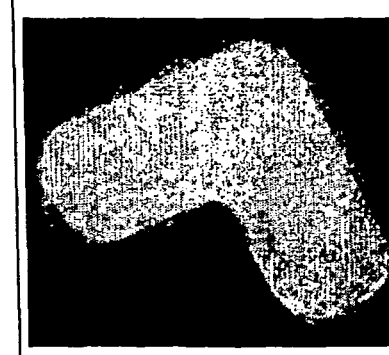 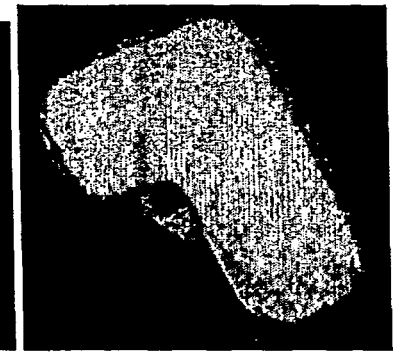

FIGURE 8A  VINCULIN
FIGURE 8B
FIGURE 8C  ACTIN
FIGURE 8D
FIGURE 8E  FIBRONECTIN
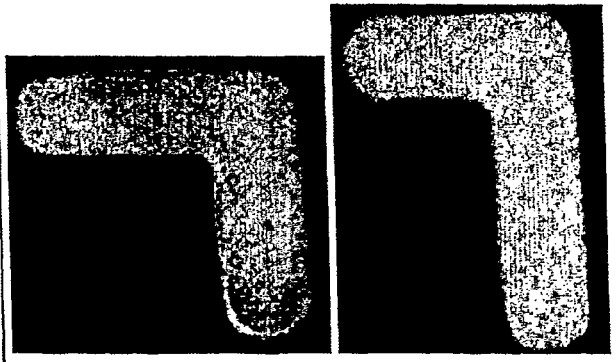

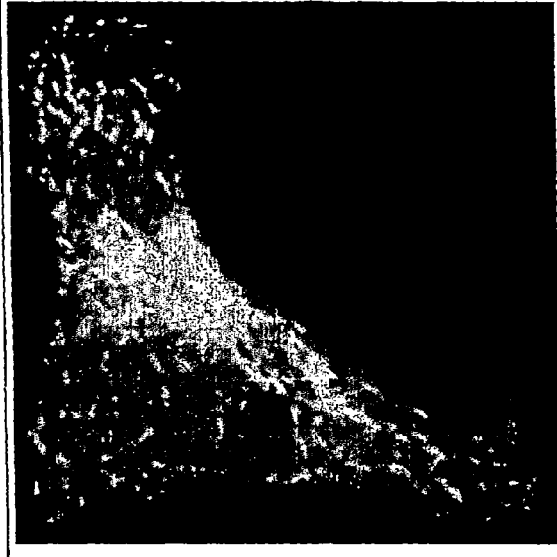
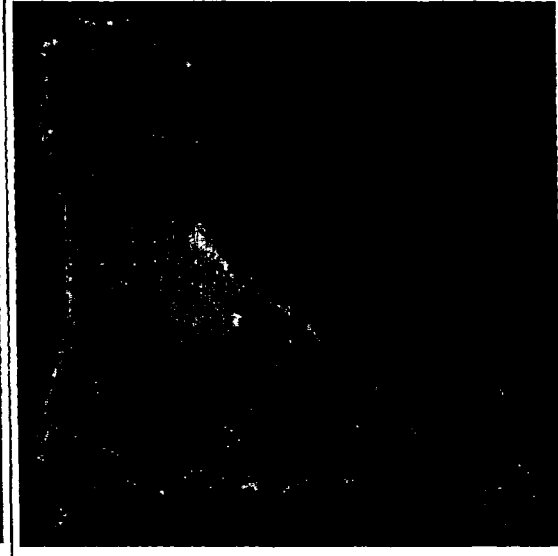

| FIGURE 12A : TGN  | FIGURE 12B : CGN  |
|---|---|
| FIGURE 12C : CENTRIN  | FIGURE 12D : FIBRONECTIN  |
| FIGURE 12E : TGN  | FIGURE 12F : CGN  |

FIGURE 13A: FIBRONECTIN
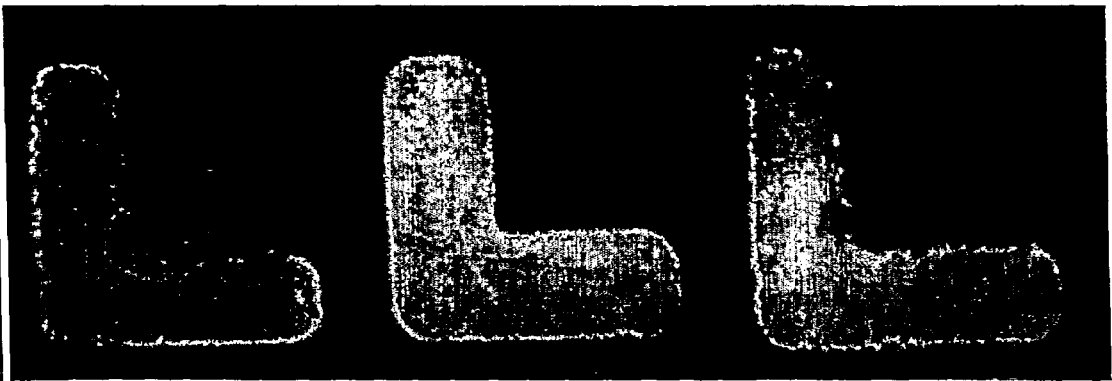
FIGURE 13B : TUBULIN
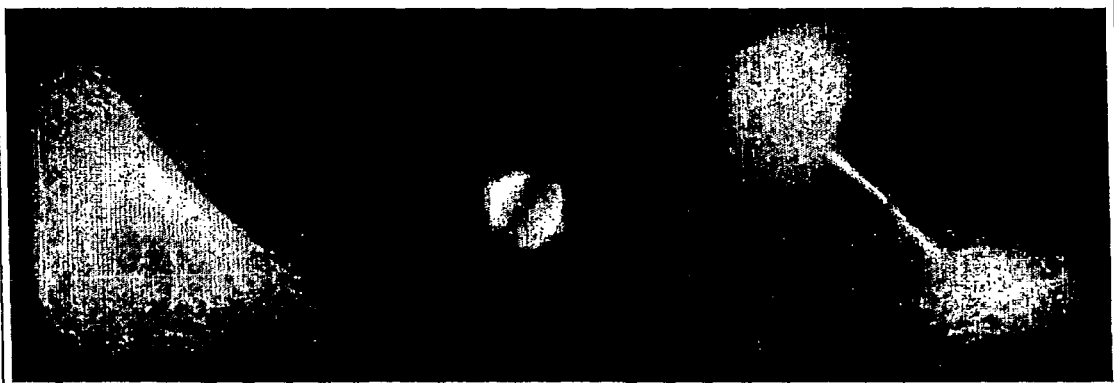
FIGURE 13C : CENTRIN

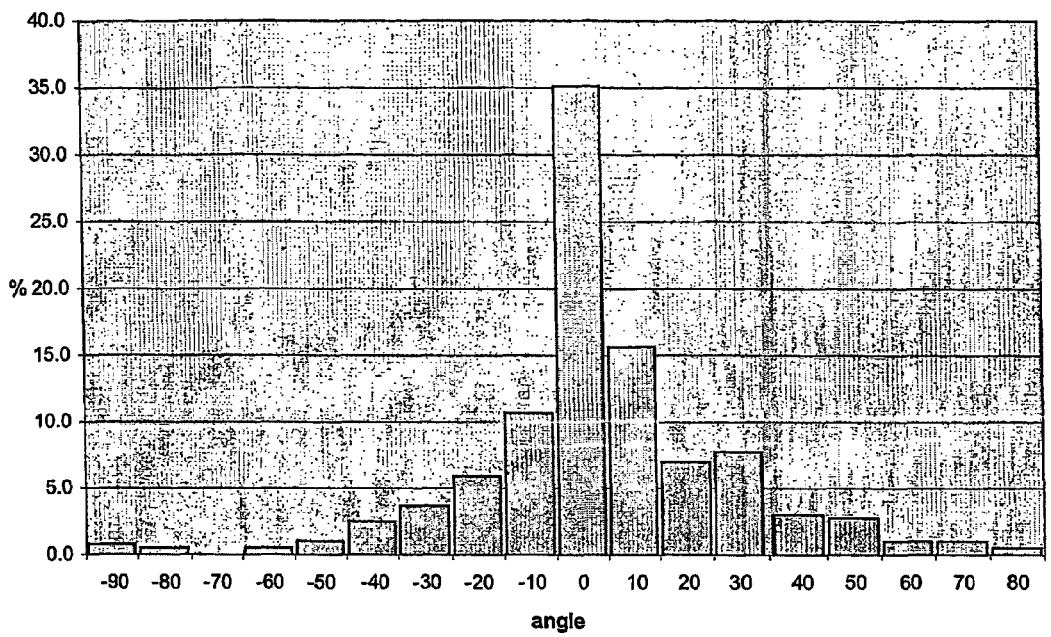
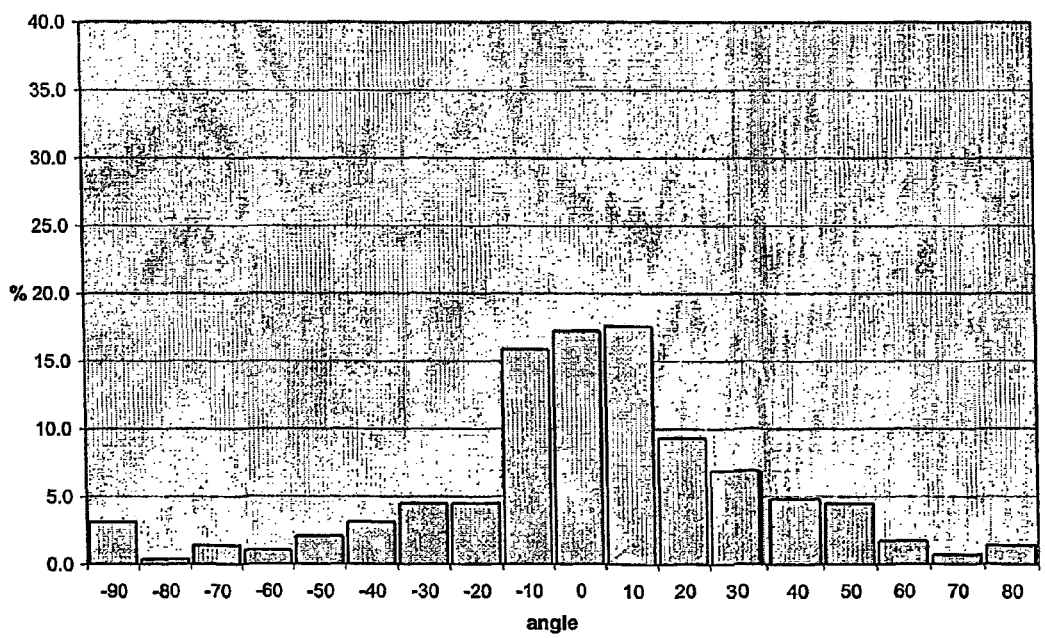

METHODS AND DEVICE FOR ADHESIVE CONTROL OF INTERNAL CELL ORGANISATION

CROSS-REFERENCE TO RELATED APPLICATION

This application is the U.S. national stage application of International Patent Application No. PCT/IB2004/003091, filed Sep. 10, 2004, the disclosure of which is hereby incorporated by reference in its entireties, including all figures, tables and amino acid or nucleic acid sequences.

FIELD OF THE INVENTION

The present invention relates to methods and devices for adhering cells in a specific and predetermined position with an adhesive control of internal cell organisation, methods for preparing such devices, methods for studying modifications of cell shape and global internal cell organization such as the distribution of cellular compartments, centrosome centering, spindle orientation, internal compartmentalization and internal transports, methods for screening compounds of interest which enhance or inhibit specific cell functions.

BACKGROUND OF THE INVENTION

High throughput cell-based phenotypic screening becomes necessary to take advantage of the wealth of data obtained from systematic genome sequencing. Genome wide gene silencing by siRNA is now possible on cultured cells. Alternatively, one would like to rapidly identify biologically active compounds from drugs libraries able to enhance or inhibit specific cell functions. The aim is thus to carry out phenotypic analyses on cultured cells with an automated tool.

High throughput methods have long been used to perform quantitative dosages on known molecular pathways. These methods cannot be used when one wants to identify new genes involved in complex cell properties like protein transport, adhesion, migration, division or apoptosis, or to probe the ability of a new drug to interfere with those mechanisms.

The challenge nowadays is to associate the accuracy of modern cell biology analysis on a small number of cells to the power of high throughput automated methods on a great number of cells. Answers to this challenge are not numerous because of several barriers:

First, the cell population on the bottom of wells has a distribution which cannot be predicted. This imposes the use of small magnification objectives or an automated but lengthy scanning acquisition.

Second, the cell shape is different from one cell to another and this parameter cannot be ignored whatever the phenotype under analysis or the quantification performed on a cell basis (intracellular localisation, number and size of particular organelles, molecular signals.).

Third, the intracellular distribution of cell compartments and the global cell organisation are also varying considerably from one cell to another. This is particularly cumbersome. It prevents any kind of precise analysis of the mutual distribution of intracellular compartments, or of the establishment and maintenance of cell polarity during cell division or cell migration.

The distribution of the cell population as well as the shape and internal organisation of individual cells, are all dependent on cell migration activity. Motility can vary largely depending on the cell type, but it is always a significant parameter.

Overcoming these difficulties would require a method to prevent cells from migrating and to orientate every cell in the same way with respect to an external clue. An answer has been provided with the micro-patterning which allows a precise control of cell shape and cell position by influencing actin assembly. Many possibilities of the micro-patterning have been investigated (Whitesides and Ingber; U.S. Pat. No. 6,368,838; WO 01/70389; WO 02/86452; WO 02/22787) but none of them influence the entire functional and structural polarity in a repetitive way compatible with a precise screening of cell intrinsic properties.

SUMMARY OF THE INVENTION

In the present invention, the inventors present an efficient and low cost method that allows the screening of genes or compounds activities on cell functions encompassing polarity, motility and division as well as internal compartmentation and transport. The method according to the invention lies on a precise control of focal adhesions distribution. These transmembranar complexes interact with the cytoskeleton which largely controls cell compartmentation. The accurate control of the intracellular distribution of each organelle is made possible by the use of an anisotropic adhesive pattern such as a concave adhesive pattern involving a non adhesive area. This control can also be made possible by the use of an adhesive pattern leading to a lengthening of the cell.

Therefore, the invention concerns methods and devices for adhering cells in a specific and predetermined position with a controlled polarisation of the internal cell organization, thereby inducing the cell machinery polarisation. The device comprises a plate defining a surface and at least one anisotropic adhesive pattern, such as a concave adhesive pattern, for an individual cell, more particularly for only one single cell, which is isolated by cytophobic regions to which cells do not adhere contiguous with said adhesive pattern.

Such devices are useful in a wide array of cellular biology applications, including cell culturing, cytometry, toxicology, drug screening, diagnosing, and immobilization of cells. They allow a high or medium throughput screening assays and/or individual assays as well.

Therefore, the invention concerns methods for preparing such devices, methods for culturing cells, methods for immobilizing cells on a surface, methods for controlling the cell shape and global internal cell organization, methods for studying cell shape and global internal cell organization such as the distribution of cellular compartments, centrosome centering, spindle orientation, internal compartmentalization and internal transports, methods for screening compounds of interest which modify, e.g. enhance or inhibit, cell shape, global organization and/or function.

LEGEND TO THE FIGURES

FIG. 1: Automated numerical detection of anaphase and spindle orientation for a cell platted on an L-shape adhesive pattern.

FIG. 1A, Frames from a 3 minutes time-lapse in phase contrast microscopy with a 10× objective. Numbers correspond to those reported on the time-curve in FIG. 1C. Mitotic cell centre indicated in frame 4 and anaphase spindle orientation shown in frame 5 are reported from the analysis b.

Figure 1B:

FIG. 1B, Wavelet segmentation of the pictures in a. Ellipsoidal fits are shown in black. Black dashed lines correspond to the major and minor ellipse axes. Mitotic cell centre is measured in frame 4, six minutes before anaphase in frame 5.

Anaphase orientation is that of the ellipse major axis in frame 5 with respect to the vertical reference of the pattern oriented as shown on FIG. 2.

Figure 1C:
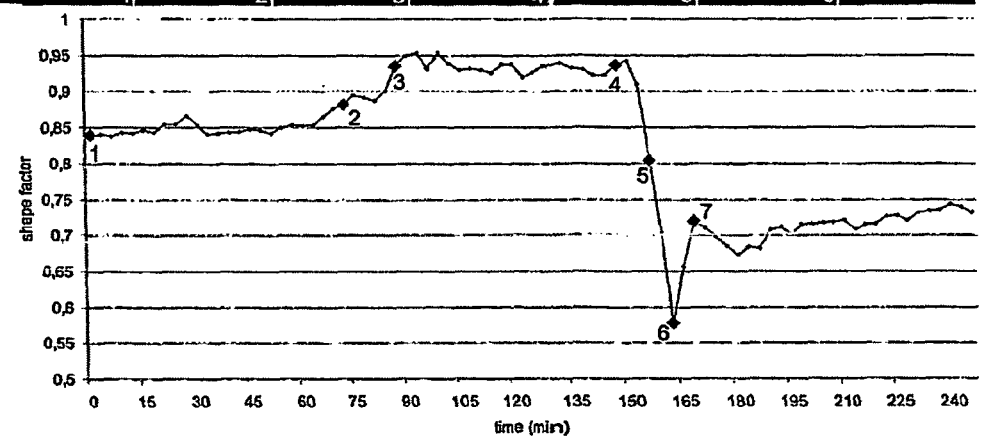

FIG. 1C, Shape factor versus time. The shape factor is the ratio of the short over the long axis defined in b. Anaphase elongation in frame 5 is automatically detected by the shape factor shift from over 0.9 to less than 0.6. Bar=20 μm.

FIG. 2: Distributions of mitotic cell positions and spindle orientations of living cells plated on various adhesive patterns. First and second columns: mitotic cell positions and spindle orientations measured as described in FIG. 1. Coordinates of the round cell centre positions are in micrometers and each bar for the mitotic spindle orientations represents 10 degrees. Third column: Examples of cells fixed in metaphase. HeLa cells expressing centrin-1 GFP plated on fibronectin micropatterns, fixed in metaphase and stained for actin (middle of the z acquisition) with phaloidin-FITC and for DNA with DAPI. Fourth column: same cells observed for actin staining with phaloidin-FITC at the bottom of the z acquisition. Note the correlation between spindle poles positioning and retracting fibers anchoring on the round cell body.

FIG. 2A-2C, Fully adhesive micropatterns of fibronectin;

FIG. 2D-2H, peripherally adhesive micropatterns;

FIG. 2I, [cross] micropattern with the same symmetries as in FIG. 2F.

Scale: cell images and cell position representations are at the same scale: grid step is 4 micrometers.

FIG. 3: Fibronectin micropatterns modulate size and orientation of the actin cytoskeleton and of focal adhesions. HeLa cells expressing centrin-1 GFP were fixed and stained in G2 (1 hour before cell rounding). Immuno labelling of vinculin, and phaloidin-FITC staining of filamentous actin on cells plated on the corresponding patterns. As a rule, actin bundles along non-adhesive borders and the corresponding focal adhesions are thicker and larger than those along adhesive borders. A 4× magnification of the bottom right corner of the merge image is shown on the right column. Note that adhesive patterns, focal adhesion distribution and actin organisation share the same symmetries and balances. FIG. 3A-I, same adhesive conditions as described in FIG. 4. Bars=5 μm.

FIG. 4: Centrosomes separation during mitotic spindle formation.

FIG. 4A-B, Cell projected area (black) and inter-centrosome projected distance (gray) versus time for cells plated on homogeneous fibronectin coated glass coverslip (FIG. 4A, n=24) or on L-shape micropatterns (FIG. 4B, n=14). Cell area is normalized with respect to the initial area. Error bar represents the standard deviation. Time 0 corresponds to the beginning of cell retraction. Centrosomes separation was more erratic but often precedes cell retraction on infinite substrate whereas it was synchronous with cell retraction on micropatterns.

FIG. 4C, An example of time-lapse acquisitions of centrin-1 GFP during mitosis on L-shape.

FIG. 4D, An example of centrosomes separation after NZ mitotic arrest. White crosses correspond to centrosomes.

FIG. 4E, Distribution of spindle orientations after NZ release. Each bar represents 30°. Note that spindles are still able to mainly orient in round cell bodies as in control cells. Bar =10μm.

FIG. 5: Examples of adhesive pattern. The black areas are indicative of the adhesive area whereas the white ones are indicative of non adhesive area.

Figure 5A:
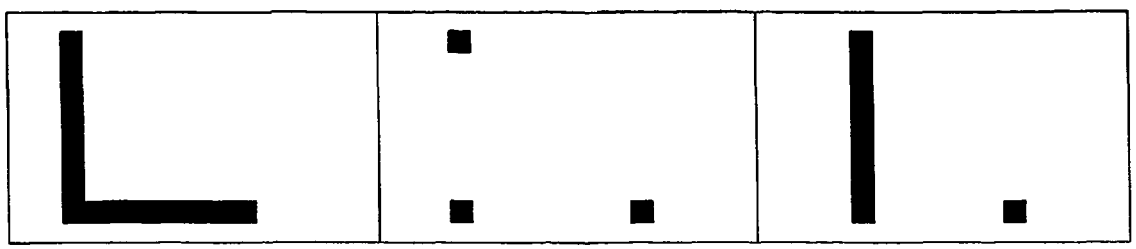

FIG. 5A: Symmetric L-shaped pattern well suited to control spindle axis orientation.

Figure 5B:
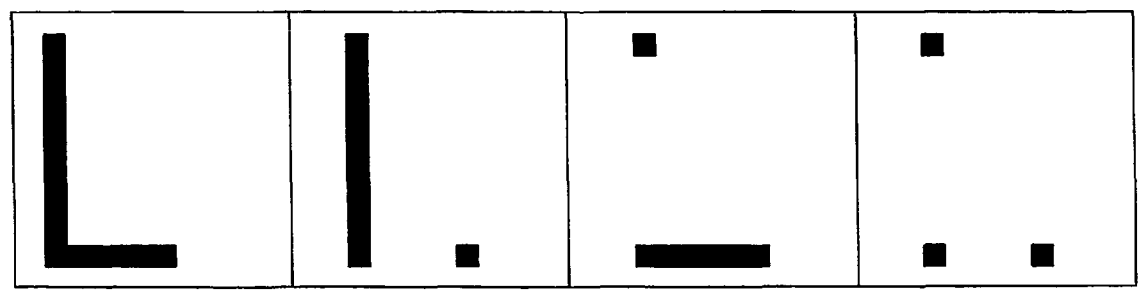

FIG. 5B: Non symmetric shapes suited to place the centrosome-Golgi apparatus organelle on one side of the nucleus.

FIG. 6: L929 cells on different L-shaped micro-patterns.

FIG. 6A: Vinculin distribution on L-shaped micro-patterns.

FIG. 6C: Actin distribution on L-shaped micro-patterns.

FIG. 6E: Fibronectin micro-patterned.

FIGS. 6B, and 6D: Vinculin and actin distribution, respectively, of control cells grown on an infinite adhesive surface.

FIG. 7: MDCK cells on different L-shaped micro-patterns.

FIG. 7A: Vinculin distribution on L-shaped micro-patterns.

FIG. 7C: Actin distribution on L-shaped micro-patterns.

FIG. 7E: Fibronectin micro-patterned.

FIGS. 7B and 7D: Vinculin and actin distribution, respectively, of control cells grown on an infinite adhesive surface.

FIG. 8: HeLa cells on different L-shaped micro-patterns.

FIG. 8A: Vinculin distribution on L-shaped micro-patterns.

FIG. 8C: Filamentous actin distribution on L-shaped micro-patterns.

FIG. 8E: Fibronectin micro-patterned.

FIGS. 8B and 8D: Vinculin and filamentous actin distribution, respectively, of control cells grown on an infinite adhesive surface.

FIG. 9: Microtubule network radiating from the centrosome towards L-Shape extremities.

FIG. 9A: EB1 labeling in a HeLa cell constrained on a L-shaped adhesive micro-pattern.

FIG. 9B: Centrin-GFP and tubulin labelling of the constrained Hela cell.

Figure 10:
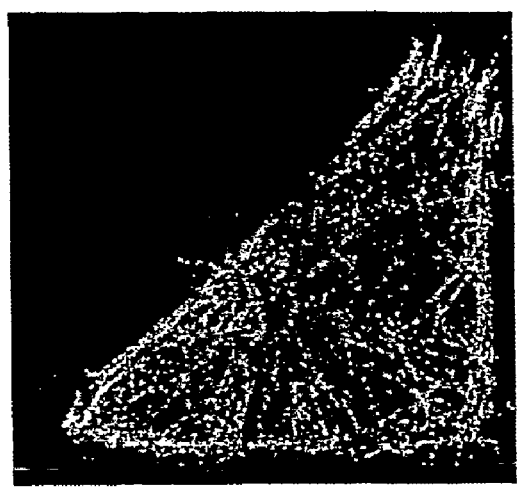

FIG. 10: Microtubule +-end trajectories from the centrosome towards L-shape extremities. EB1 dynamics measured by video-recording in HeLa cells transfected with EB1-GFP. Superposition of time-lapse acquisitions every 2 seconds during 2 minutes.

Figure 11:
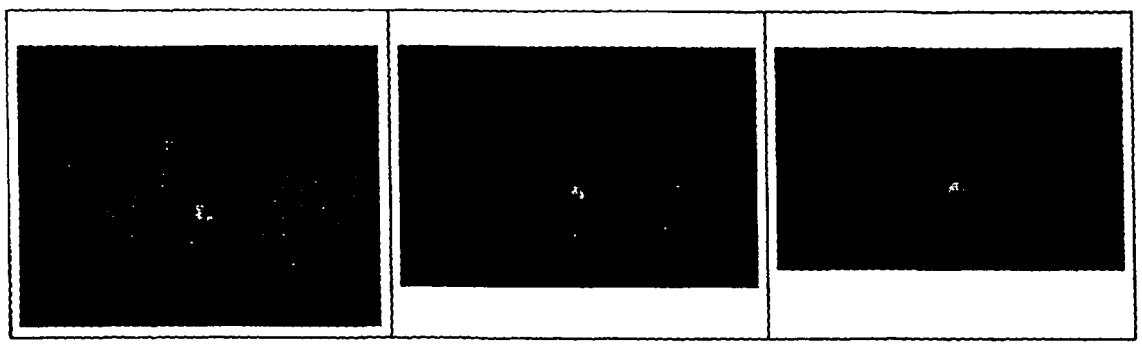

FIG. 11: Centrosome position: HeLa cells stably expressing Centrin1-GFP were video-recorded during 4 min. Superposition of time-lapse acquisitions every 4 s. Fibronectin in gray, centrin in white.

FIG. 12: A, B, C, D: Golgi concentric structure around the centrosome of an Hela cell on L-shaped micro-patterns.

FIG. 12A: Immunolabelling for TGN (Trans Golgi Network);

FIG. 12B: Immunolabelling for CGN (Cis Golgi Network);

FIG. 12C: Centrin GFP; and

FIG. 12D: Immunolabelling for micro-patterned fibronectin.

FIG. 12: E, F: Golgi structure for a cell grown on an infinite adhesive surface.

FIG. 12E: Immunolabelling for TGN (Trans Golgi Network);

FIG. 12F: Immunolabelling for CGN (Cis Golgi Network).

FIG. 13: Hela cells fixed on an L-shape micro-patterns showing three different stages of the mitosis: interphase, metaphase and post-telophase.

FIG. 13A: micro-pattern of fibronectin;

FIG. 13B: Immunolabelling for tubulin;

FIG. 13C: Centrin GFP.

Figure 14:
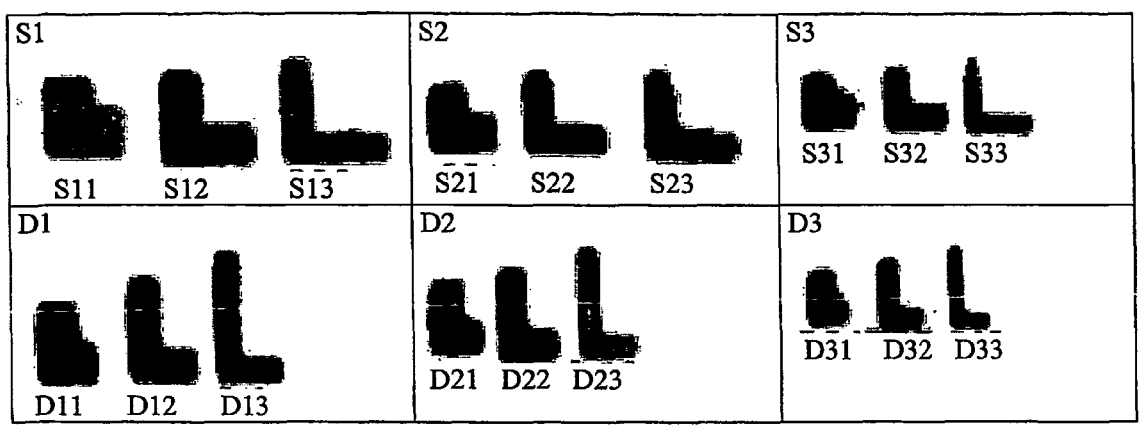

FIG. 14: Different L-shaped adhesive micro-patterns: in each zone, the total adhesive surface remains constant, the branches getting thinner and longer. From S1 or D1 to S3 or D3, the adhesive surfaces decrease.

Figure 15:
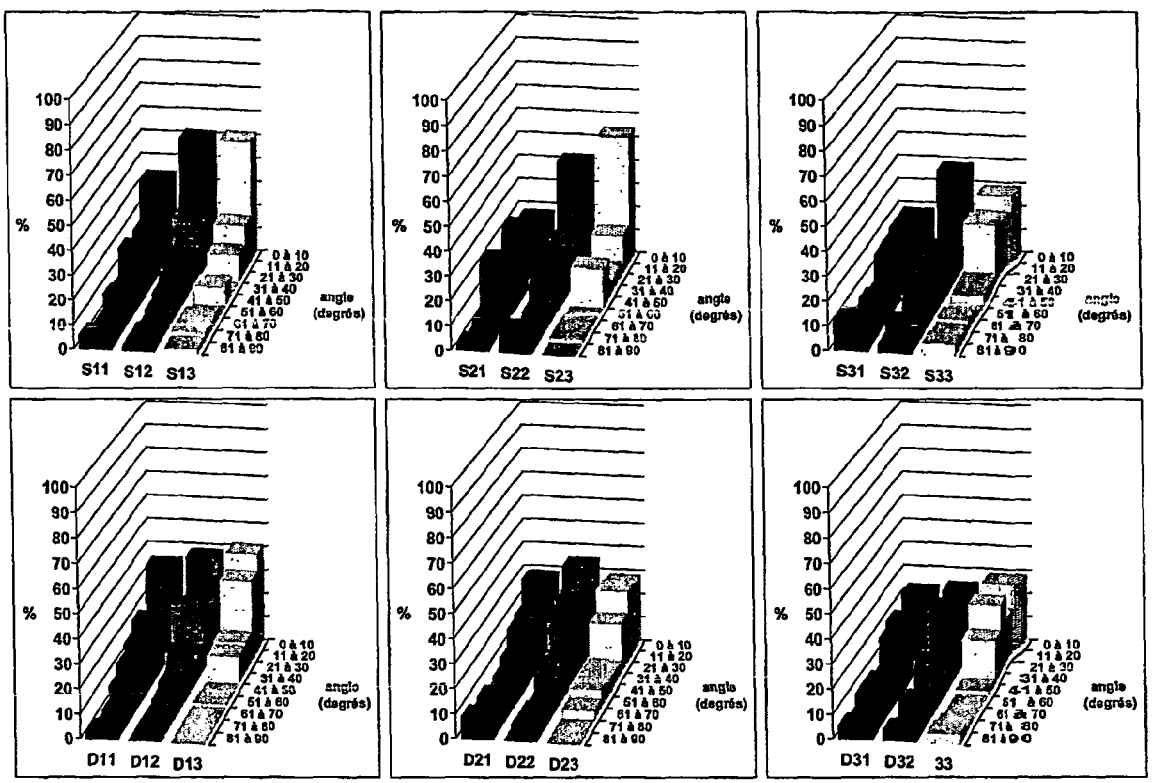

FIG. 15: Distribution curves of the angle between the metaphase plane and the normale (perpendicular) to the L hypotenuse. Number of measurements per curve≈50.

Figure 16:
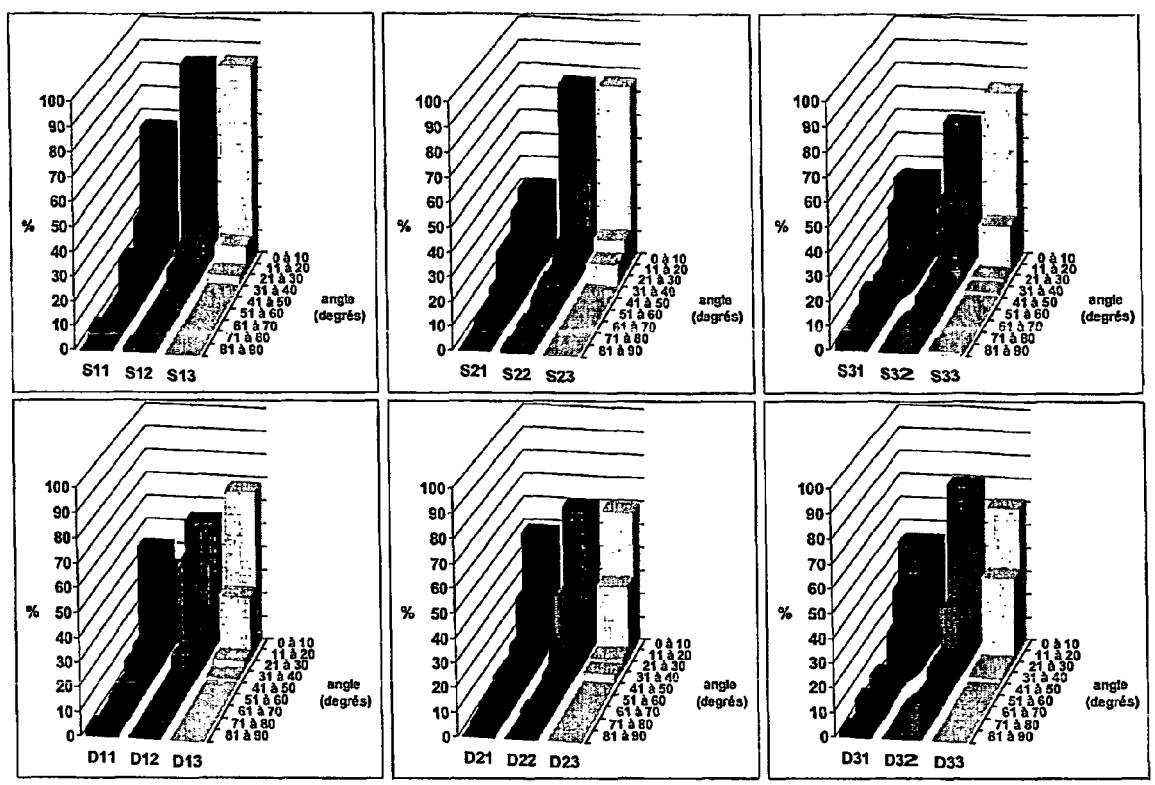

FIG. 16: Distribution curves of the angle between the cell division axis during telophase and the L hypotenuse. Number of measurements per curve≈50.

FIG. 17: Distribution curves of the angle between the metaphase plane and the normale (perpendicular) to the L, or the corresponding full triangle hypothenuse.

FIG. 17A: Distribution curve on an L shape (S13 in FIG. 16);

FIG. 17B: Distribution curve on the corresponding full triangle.

DETAILED DESCRIPTION OF THE INVENTION

The approach according to the invention rests on the property of cells from most animal tissues to be convex and to display a stereotyped distribution of intracellular compartments with respect to specialized contacts with neighbour cells which prevent their migration.

Indeed, cell-cell or cell-ECM interactions in tissues induce the segregation and spatial organisation of membrane adhesive proteins. The internal cell structure and organisation are linked to these boundary conditions. Signalling cascades control cell activity from peripheral receptors but also from mechanical stimuli at adhesion sites. At any moment, the adhesive pattern of a cell is the outcome of the cross-talk between cell activity, which controls the plasma membrane structure and composition, and cell dynamic response to the constraints of the environment.

In classical culture conditions on infinite adhesive planes, cell adhesive structures like focal adhesions (FA) or focal complexes are distributed all over the 'ventral' cell contact area to the substrate, although in a non homogeneous manner. The ability of cells to develop tension between adhesive complexes is an important parameter of their geometry: at any moment, the cell shape corresponds basically to the convex envelope of the most distal adhesive contacts. This property can be used to control cell shape: controlling the distribution of adhesive complexes suffices to impose the shape of cells not only on a non-infinite adhesive surface but even on non-connected surfaces.

This property can even be observed ex vivo with epithelial cells, for example with enterocytes or kidney cells, when their polarity is normalized by culture conditions (two compartments chambers). The use of such culture conditions for high throughput analysis is however limited.

A more physiological approach for fibroblastic cells is to grow cells in 3D collagen gel fibers. The use of such culture conditions for high throughput analysis is however limited.

An alternative approach compatible with high throughput analysis is to offer a limited pattern of possible contacts on a 2D surface: in this way, one can force cells to adopt a behaviour similar to that of cells in tissues in response to limited contacts with neighbour cells.

As coverslips are infinite adhesive planes which impose a uniform and non physiological environment, micropatterned cell-sized surfaces like squares and other regular polygones are a first step towards mimicking a mechanical constraint from the environment on cell migration and cell organisation. These surfaces only limit the extent of cell flattening however. They still create a very large connected adhesive surface with respect to the cell size, which imposes 'dorsal' and 'ventral' domains to the cell plasma membrane, quite different from the limited number of contacts that cells establish with neighbourg cells in tissues.

The inventors demonstrate for the first time that cells interpret the topology of the adhesive pattern by assembling an actin network that exerts a non-isotropic field of traction forces on adhesive contacts. This drives the orientation of the bipolar spindle at the onset of mitosis. Therefore it is not cell shape but cell adhesion that can determine the cleavage plane.

The inventors further demonstrate that cells respect precise rules in response to their adhesive contacts, which in turn affects the orientation of cell division. These adhesive contacts also pass on a positional memory to the daughter cells. They report the first device, using adhesive micro-patterning, to reliably control the division axis of animal cells in culture. Preferably coupled to automated monitoring, it should be of considerable value for analyzing the cell mitotic process and its perturbations in high throughput screenings.

The principle of the present invention, which is called herein adhesive control of internal cell organisation (ACICO), is to create a network (an array or a grid) of adhesion (anchoring) surfaces for individual cells which prevent them from migrating and allow a reproducible polarisation of the cell machinery in which the position of the different organelles, like the centrosome or the Golgi apparatus, can be predicted.

The unit motive or pattern of the network is an anisotropic adhesive surface. This anisotropic adhesive surface induces a disequilibrium in the adhesion sites which leads to a cell polarisation. More particularly, a preferred anisotropic adhesive surface is such that at least one side of the adhering cell should have no contact with the adhesive surface. The disequilibrium in the adhesion sites can be, for instance, observed through the actin filaments which are inhomogenously distributed at the cell outline. This disequilibrium can also be observed through the number of retracting fibers attachment (RF). For example, the presence of only two RFs attachments leads to an excellent cell polarisation. An anisotropic adhesive surface can design by limiting the number of symmetry elements of the pattern and by biasing their respective weights. Preferably, the adhesive pattern according to the present invention has 1 or 2 axis of symmetry, more preferably only one axis of symmetry.

A preferred anisotropic adhesive surface according to the present invention is a concave or hollow adhesive surface: its convex envelope will impose the casting surface of an individual cell in spite of a large non adhesive area. Once cells are stabilized on these patterns, the limited number of adhesive contacts of each individual cell with the substrate and the distribution of these contacts according to a concave, or hollow, motive, induce the reproducible polarisation of the cell machinery. In the present application, the term "concave adhesive pattern" refers to an adhesive pattern which presents a convex envelop, said envelop includes at least 5% of non-adhesive area, preferably 10, 20 or 30%. By "convex envelope" is intended the minimal convex polygon containing the adhesive pattern.

In an alternative and less preferred embodiment of the present invention, the adhesive pattern is a pattern which leads to a lengthening of the cell. Indeed, the lengthening of the cell can polarized the cell. This pattern leads to an outline shape factor (SF)or presents a shape factor which is less than 0.6, preferably less than 0.5, more preferably less than 0.4). In a preferred embodiment, said adhesive pattern is a long and thin adhesive area, for instance a rectangular area or the like. The shape factor is the ratio between the small axis and the large axis of an ellipse fitted on the cell outline or on the envelope of the adhesive area. The long and thin adhesive area according to this embodiment can have various forms such as a rectangle, a diamond or a cross.

The invention concerns a device for adhering at least one cell, preferably in a specific and predetermined template, with a controlled polarisation of the internal cell organization, comprising:
- a plate defining a surface; and,
- at least one anisotropic adhesive pattern on said surface,
  - wherein the size of said pattern is such that only one individual cell can adhere in said pattern with a controlled polarisation of the internal cell organization; and,
  - wherein the anisotropic adhesive pattern is either a concave adhesive pattern or a long and thin adhesive area with a shape factor of less than 0.6.

Preferably, said device comprises a plurality of adhesive patterns isolated from each others by cytophobic regions to which cells do not adhere. More particularly, said device comprise at least 2 adhesive patterns, preferably at least 5, 10, 100, 1 000, 10 000, or 100 000 adhesive patterns. In a preferred embodiment, said device comprises between 10 and 50 000 adhesive patterns/cm$^2$, more preferably between 5 000 and 15 000 adhesive patterns/cm$^2$, still more preferably about 10 000 adhesive patterns/cm$^2$.

According to the present invention, the form of the adhesive pattern allows the reproducible polarisation of the cell machinery. In a most preferred embodiment, said anisotropic adhesive pattern is a concave adhesive pattern. In a less preferred embodiment, said adhesive pattern is a long and thin adhesive pattern which induces a lengthening of the cell, with an outline shape factor (SF) which is less than 0.6, preferably less than 0.5, more preferably less than 0.4.

The cytophilic island comprises preferably a concave adhesive pattern involving non adhesive area. For example, the adhesive surface can have the form of the following letters: C, L, U, V. In a most preferred embodiment, the concave adhesive pattern has the [L] form.

The inscribed surface by the concave adhesive pattern comprises adhesive and non-adhesive area and the convex envelope of said concave adhesive pattern comprises preferably one or several adhesive area, more particularly one or several adhesive lines or curves. In a particular embodiment of the present invention, the convex envelope of the concave adhesive surfaces is a polygon. Preferably, said polygon also comprises at least one adhesive edge. Said polygon can be a triangle, a quadrileral, a pentagon, a hexagon, a heptagon, an octagon. a nonagon, a decagon, a hendecagon, a dodecagon, a pentadecagon or an icosagon.

For example, the polygon consists of one or several adhesive edge(s) and, optionally, one or several adhesive corner(s). Examples of adhesive pattern are also illustrated in FIGS. 2D, 2E, 2G, 2H and 5.

If the polygon is a triangle, the polygon can have for example either one adhesive edge and one adhesive corner (i.e., [bar+dot] form), or two adhesive edges (e.g., [L] form).

If the polygon is a quadrileral, the polygon can have for example:
- one adhesive edge and two adhesive corners (i.e., [bar+2 dots] form);
- two non-consecutive adhesive edges (e.g., [twin bars] form);
- two consecutive adhesive edges and one adhesive corner (e.g., [L+dot] form); and
- three consecutive adhesive edges.

Said quadrilateral can be a regular or unregular quadrilateral. It can be for example selected from the group consisting of a square, a rectangle, a diamond, and a trapezium.

In a preferred embodiment, said polygon is a triangle. More particularly said triangle has two adhesive edges. Preferably, the angle between the two adhesive edges is between 30 and 150°, more preferably between 60 and 120°, still more preferably about 90°. Preferably, the length ratio of the two edges is between 0.1 and 1, more preferably between 0.3 and 1, still more preferably between 0.5 and 1. For the analysis of cells in mitosis, the length ratio of the two edges is preferably about 1. For the analysis of cells in interphase, the length ratio of the two edges is less than 1, more preferably between 0.3 and 0.8.

The adhesive pattern can be formed of single connected adhesive surfaces and/or of non-connected adhesive surfaces. In a particular embodiment, the adhesive pattern can be formed either of a single connected adhesive surface or of several non-connected adhesive surfaces. By "single connected adhesive surface" is preferably intended a solid line or curve. By "non-connected adhesive surface" is preferably intended dotted or dashed line or curve, or discrete point or area. In a preferred embodiment, the adhesive pattern consists of a combination of adhesive elements selected from a line, a curve and a point.

The width of the adhesive point, lines, curves or edges is preferably between 0.1 to 10 μm, more preferably between 1 to 5 μm, still more preferably about 4 μm.

In a preferred embodiment, the inscribed surface by the adhesive pattern is mainly non-adhesive, preferably essentially non-adhesive. More preferably, the inscribed surface by the adhesive pattern is completely non-adhesive. Optionally, 75% of the inscribed surface by the adhesive pattern is non adhesive, preferably 90%, more preferably 95%, still more preferably 99%.

Preferably, the ratio between the adhesive area and the non-adhesive area of the convex envelope of the adhesive pattern is the lowest consistent with the cell flattening. For example, the ratio is between 10 and 90%, preferably between 20 and 80%, still more preferably between 30 and 70%.

The size of the adhesive pattern is such that an individual cell is able to adhere thereto. Preferably, the size of the adhesive pattern is such that one single cell could spread and divide, but restricted cell movement. Preferably, the area of the convex envelope of the adhesive pattern is between 1 and 2,500 μm$^2$, more preferably between 1 and 1,000 μm$^2$, still more preferably between 1 and 500 μm$^2$ or 500 to 900 μm$^2$. The size of the adhesive pattern depends on the cell type.

The surface of a plate comprises a plurality of discrete adhesive patterns, each of which promote adherence of an individual cell, arrayed in a predetermined geometric template, the adhesive patterns being isolated one from another by cytophobic regions which do not promote adherence of cells. The cytophobic regions are sufficiently wide to prevent cells adhered to said adhesive patterns from contacting each other. Preferably, the mesh of the network is larger than two cell diameters. Preferably, the adhesive patterns are separated by at least 10 μm, preferably by at least 20, 30, or 50 μm.

The adhesive pattern comprises molecules that promote cell attachment. These molecules are well known to those of ordinary skilled in the art and comprise antigens, antibodies, cell adhesion molecules, extracellular matrix molecules such as laminin, fibronectin, synthetic peptides, carbihydrates and the like. Preferably, said adhesive patterns comprise extracellular matrix molecules, more preferably fibronectin.

The non adhesive surface is an inert surface. An appropriate inert surface is a surface covered by a derivative of oligo or poly(ethylene glycol).

The plate is a support convenient for confocal, optical and/or fluorescence microscopies. In the more preferred embodiment, the plate is glass, preferably silanised glass. For example, a convenient plate according to the present invention is a coverslip or a slide.

The device according to the present invention can comprise several groups of adhesive patterns on the same plate separated from each other such that each group can be incubated in a different medium. For instance, a group of adhesive patterns can be contacted with a test compound and an other group can be contacted with another test compound or without any test compound. This separation can be provided by a physical barrier such as teflon seal. For example. see SPI Teflon® Teflon of SPI Supplies, Teflon® Printed Slides of Aname.

The device according to the present invention with adhesive patterns and the cytophobic regions are formed by micropatterning, preferably by microcontact patterning. Standard methods are well known by those skilled in the art. For review, see Whitesides et al (Annu. Rev. Biomed. Eng., 2001, p. 335-373, more particularly p. 341-345).

The invention concerns a method for preparing a device according to the present invention, said method comprising:
preparing a master template with at least one adhesive pattern;
preparing a stamp from said master template;
inking said stamp with molecules that promote cell attachment;
contacting the inked stamp with the plate;
making cytophobic the non-printed surface of the plate.

Preferably, the master template is prepared from a silicon wafer coated with a photoresist layer by illuminated with UV through a mask on which the adhesive pattern has been designed. The stamp is preferably poly(dimethylsiloxane) (PDMS) or another siloxane-based polymer. Preferably, said non printed surface of the plate are made cytophobic by an incubation with an inert material such as polyethyleneglycol.

A particular example of the preparation of a plate according to the present invention is detailed the example section.

The micropatterning allows a precise control of cell position at micron scale. The use of glass coverslips without any gold or other metals coating is compatible with every optical imaging technics and especially with epifluorescence on an inverted microscope for video-microscopy. The automation of many 4D acquisitions (3D in time-lapse) is very easy : with a motorised XY stage, one only needs to record the XY position of the first cell as all the others can be deduced from the first one by a known iterative translation; a 100× objective on a ceramic piezoelectric device makes the 3D stack acquisition very fast. Glass coverslips and micropatterning allow ones to perform high throughput 3D cell screening at high magnification using epifluorescence as well as transmitted light. When cells are synchronized before seeding, one can get at the description of a "mean cell" by summing the observation of as many cells necessary. It provides a very accurate description of cell organization or behaviour as cells are very similar if not identical. From such a "mean cell" description, one can place adequate thresholds for screening active drugs on a particular cell function or genes whose inactivation impairs that function.

Accordingly, the invention further comprise an automated method of analysis for detecting the position and the orientation of cells in the course of time and at the precise moment of cell division. This method comprises:
a) identifying the position of adhesive patterns on the plate;
b) recording cell images at several times for several identified patterns;
c) fitting an ellipse on the cell outline from cell images;
d) detecting the division time and determining the parameters of interest.

In a preferred embodiment, the method comprise in step d) the step of calculating the rounding of the cell (as indicated below). The evolution of the rounding according to time allows the determination of the moment of the cell division and the spindle orientation. Preferably, the spindle orientation is determined during the lengthening phase.

More particularly, this method comprises:
1—identifying the position of adhesive patterns on the plate using fluorescence;
2—recording phase contrast images (transmitted light) at several times for several identified patterns;
3—preferably, segmenting phase contrast images by wavelet decomposition;
4—fitting an ellipse on the segmented images;
5—detecting the division time and determining the parameters of interest.

The step 1 is carried on a 2D fluorescent image of the plate. On this plate and according to the objective of the microscope, one observes various rectangular areas (fields) including several adhesive patterns. The adhesive patterns detection is preferably performed by correlation analysis with a 2D Fourier transform.

In the step 2, the detected positions of the adhesive pattern are used for recording temporal sequences (2D images according to time) on the different fields and for each adhesive pattern. The images are phase contrast images (transmitted light). At this stage, it is possible to determine if a cell has adhered on the pattern.

In the step 3, the cell is segmented in order to separate the cell from the background. This segmentation can be performed through a wavelet decomposition transform. The wavelet decomposition transform allows to keep only a part of the details present in the initial image. Therefore, the too small details (which can be considered as background noise) or the too thick details (which can be considered as fluctuation of background) are removed. In the obtained image, a threshold to separate the pixels assimilated to a physical structure of the pixels assimilated to the background is used. An algorithm of segmentation of the detected structures is used to delimit the related structure representing the cell.

In the step 4, an ellipse is fitted on each segmented cell by a principal components analysis (thus minimizing the average quadratic error). The temporal sequence of images is thus comparable with a set of ellipses centered on the center of mass of the segmented structures, the form (small and large axis) and the orientation of the ellipse reproduce the morphology of the cell as well as possible. One of the form parameters is the rounding (SF) which is the ratio between the small axis and the large axis of the ellipse. For example, when the ellipse is a circle, the rounding is 1 and when the ellipse is a line, the rounding is 0. The orientation parameter is the angle between the large axis and a horizontal or vertical reference. Indeed, it can be assumed that the orientation of the large axis of the ellipse during the lengthening step is the same that the spindle orientation.

In the step 5, the temporal analysis of the rounding of a cell allows the automated detection of the moment of the cell division. The different stages of the cellular cycle induce a particular behaviour of the form parameter. During the mitosis, the cell becomes round (rounding almost 1). Then, at the anaphase, the cell lengthens suddenly (the rounding decreases quickly). One seeks to find the moment exact separating the round phase from the phase of lengthening. Therefore, for each time t, one tests if the few last moment (e.g. t−6 to t−1) are overall higher than a first threshold (specific to the round phase), then one tests if the few future moments (e.g. t+1 with t+5) are overall lower than a second threshold (specific to the phase of lengthening). In the affirmative of these two conditions, one considers that the moment T defines the beginning of the anaphase. For more details, see FIG. 1 and Example 1.

This automated method allows to deal with higher volumes of data and therefore to perform statistic analysis. Moreover, the morphology analysis of the cells according to time and during cell division is more reproducible and therefore leads to more reliable results.

Parameters of interest are preferably selected in the group consisting of the mitose duration, the duration of the phase of entry into mitose (G2-mitose transition phase), the duration of the mitose end phase (abruptly or gradually) or and the orientation of the spindle orientation. The spindle orientation is one very interesting aspect among the determined parameters.

The device according to the present invention can be useful in a wide array of cellular biology applications, both in fundamental and applied research field, including cell culturing, cytometry, toxicology, drug screening, immobilization of cells. This device is well appropriate to study the shape, the global internal organization, the internal transport and some cellular functions of cells, preferably the mitosis.

Therefore, the invention concerns a method for culturing at least one cell on a surface or in a medium on a surface, said method comprising:
    providing a plate defining a surface and at least one adhesive pattern according to the present invention, preferably a device according to the present invention; and,
    culturing the cells on said adhesive pattern(s) or in a medium on said adhesive pattern(s).

The medium can be any medium convenient for the cell culture. For instance, the medium can be Dulbecco Modified Eagle Medium with 10% calf serum, 1% penicillin and streptoycine and 1% glutamine.

The invention also concerns a method for immobilizing at least one at a surface, said method comprising:
    providing a plate defining a surface and at least one adhesive pattern according to the present invention, preferably a device according to the present invention; and,
    exposing the plate to at least one cell for a period of time sufficient to allow the cell(s) to bind to said adhesive pattern(s).

The invention further concerns a method for studying the shape, the global internal cell organization, and/or a function of a cell, said method comprising:
    providing a plate defining a surface and at least one adhesive pattern according to the present invention, preferably a device according to the present invention;
    contacting said adhesive pattern(s) with at least one cell for a period of time sufficient to allow the cell(s) to adhere to the adhesive pattern(s);
    growing the cell(s) on the adhesive pattern(s); and,
    observing the shape, the global internal cell organization, the mitosis, and/or a function of said cell(s).

In a particular embodiment, the global cell organization is evaluated through, but not limited to, the observation of the centrosome position, the Golgi apparatus structure (i.e. CGN and TGN), the network of vinculin, actin (e.g., the spatial distribution of actin filaments), and/or tubulin, the internal transport of molecule, or the spindle orientation.

In another embodiment, the method comprises an automated analysis of said cell(s) using an image analyzer including a specific software using an algorithm designed for such analysis. More particularly, the specific software allows to perform the automated method described above.

Any kind of cell can be used in the present invention. Preferably, the cell is eukaryotic. Cell can be from animal, mammalian, human, or plant. Cell can be for example fibroblast, and hematopoietic, endothelial and epithelial cell. Cell can be derived from a healthy or pathologic tissue or organism. The cell can be wildtype or modified cells. In a particular example, the cell can be a tumor cell. For example, a gene can be inactivated and these methods allow to identify the genes which are involved in the cell shape, in internal cell transport of molecules, in the global internal organization, in the compartmentation, in the spindle formation or orientation etc.

The present invention further concerns a method for determining if a cell has a transformed phenotype associated to a spindle misorientation. It can be an interesting criteria for determining if the cell is a cancer cell. The method can comprises:
    providing a plate defining a surface and at least one adhesive pattern according to the present invention, preferably a device according to the present invention;
    contacting said adhesive patterns with cells to test for a period of time sufficient to allow the cells to adhere to the adhesive patterns;
    growing the cells to test on the adhesive patterns; and
    determining the spindle orientation for each cell and comparing the spindle orientation of different cells;
    a large spindle orientation dispersion indicating that the tested cell has a transformed phenotype associated to a spindle misorientation.

A large spindle orientation dispersion is estimated in comparison with the spindle orientation dispersion for normal cells. Preferably, a large spindle orientation dispersion is an angle variation of at least of 20°, more preferably at least of 30, 40 or 50°.

The invention concerns the use of a device according to the present invention for screening compounds of interest which modifies the cell shape, the global internal organization of the cell, the mitosis, or a function of the cell. The invention also concerns the use of a device according to the present invention for identify genes of interest which are involved the cell shape, the global internal organization of the cell, the mitosis, or a function of the cell. The invention further concerns the use of a device according to the present invention for determining if a cell has lost its ability to control a proper orientation of the spindle.

The invention further concerns a method for screening compounds of interest using the device according to the present invention. Indeed, this device allows high-throughput screening since the shape and the global internal organization of the cells are reproducible and rugged and the results record can be automated. This device allows to observe the effect of the test compounds on the cell shape, on the global internal organization of the cell or on a function of the cell.

More particularly, the invention concerns a method of selecting biologically active compounds, said method comprising:
    providing a device according to the present invention;
    contacting said adhesive patterns with at least one cell for a period of time sufficient to allow the cell(s) to adhere to the adhesive patterns;
    contacting a test compound with said cell(s);
    growing the cell(s) on the adhesive patterns; and,
    observing the shape, the global internal cell organization, the mitosis, and/or a function of said cell(s).

In an alternative embodiment of the screening method, the cells can be grown on the adhesive patterns before to be contacted with the test compound. Thus, it can be possible to evaluate the effect of the compound on the existing shape and organization of the cell.

Preferably, the method comprises an additional step of comparing the shape, the global internal cell organization and/or a function of said cell(s) with cells not contacted by said test compound. Optionally, said control cell can be contacted with a reference compound with known effect.

The test compound may be of various origin, nature and composition. It may be any organic or inorganic substance, such as a lipid, peptide, polypeptide, nucleic acid, small molecule, etc., in isolated or in mixture with other substances. For instance, the test compound can be an antibody, an antisense oligonucleotide, or an RNAi. The compounds may be all or part of a combinatorial library of products, for instance.

For example, compounds of interest can be compounds that inhibit or block mitosis or cell migration or that induces apoptosis. These compounds are useful for the treatment of cancer.

In Non Dividing Cells, or During the Interphase of Dividing Cells

The presence of a non adhesive area under the cell induces a reproducible cell type-specific distribution of adhesive structures and actin filaments. Because of the permanent interaction between the different components of the cytoskeleton, the localisation of FA (Focal Adhesion) influences membrane protrusions where actin polymerizes as well as the dynamic organisation of the microtubule network, including the position of the centrosome where microtubules are nucleated. The whole Golgi structure at the center of the protein taffic, which is classically localised at the vicinity of the centrosome, is polarized from CGN (Cis Golgi Network) to TGN (Trans Golgi Network) not only locally, as observed in classical culture conditions, but globally, at the whole organelle level. The Golgi apparatus is no longer distorted by cell flattening, but displays a concentric organization of the various compartments about the centrosome. This allows an easy comparison of the Golgi structure or activity from one cell to another. Similarly, it is very easy to probe drugs or genes which would have an effect, even a small one, on the position the centrosome, whereas it is very difficult if not impossible to do it in classical culture conditions.

Cell Division and Mitotic Spindle Orientation

A very controlled orientation of the spindle axis can be obtained. The orientation of the metaphase plane and the tension between daughter-cells during cytokinesis are very precisely induced by the proposed adhesive patterns. Cell divisions are thus controlled in space and time in a way which allows precise and quantitative comparisons between individual cells, and between cell types, either control or transformed cells. It is particularly convenient for the evaluation of drug effects, but can be used as well for gene inactivation analysis.

Further aspects and advantages of the present invention will be disclosed in the following experimental section, which should be regarded as illustrative and not limiting the scope of the present application.

EXAMPLES

Example 1

Methods
Micropatterns Fabrication

Microcontact printing is a fully described method (Whitesides et al, *Annu. Rev. Biomed. Eng.*, 2001, p 335-373). We made the poly-dimethyl siloxane (Sylgard, Dow Corning) stamps using a method described by Dr. A. Pépin (Pépin, A., Chen, Y., in *Alternative lithography* (ed. Sotomayor Torres C. M.) 305-330, Boston/Dordrecht/London, 2003). The glass coverslip treatment we used has been developed by Dr P. Nassoy (Cuvelier et al. *Eur. Biophys. J.* 32, 342-354 (2003). A stamp was inked with a 50 µg/mL fibronectin solution, 10% of which was labelled with Cy3 (Amersham Biosciences), for 5 minutes, dried and placed in contact with a silanised coverslip for 5 minutes. After removal of the stamp, the printed coverslip was immersed in PBS containing 20 mg/mL maleimide-poly(ethyleneglycol), PEG-mal (Nektar Therapeutics) for 1 hour at room temperature. The coverslip was then gently washed in PBS ready for cell deposition.

Cell Culture and Deposition

HeLa, human epithelial cells, stably expressing centrin1-GFP (Piel et al. *J. Cell Biol.* 149, 317-329 (2000), were cultured in Dulbecco Modified Eagle Medium with 10% foetal calf serum, 1% penicillin and streptomycin, and 1% glutamine at 37° C. Cells were synchronised using a double thymidine block and then removed from their flask using VERSEN, 10 minutes at 37° C. After removing the VERSEN by centrifugation, cells were resuspended in DMEM with 1% FCS and deposited on the printed coverslip at a density of $10^4$ cells/$cm^2$.

Fixation and Staining

Premitotic cells were permealised with 0.5% TritonX-100 in cytoskeleton buffer (CB) (Mitchison. *Cell Motil. Cytoskeleton* 22, 135-151 (1992)) for 2 minutes and then fixed in paraformaldehyde 4% in CB for 20 minutes and treated with ammonium chloride 0.1 M for 10 minutes. Cells in metaphase were fixed using a method described by Mitchison (1992) which preserves retracting fibers. Actin and DNA were stained using phaloidin-FITC and DAPI. Vinculin was immunolabelled with primary mouse antibodies provided by Dr M. Glukhova and secondary Cy5-conjugated goat anti-mouse antibodies (Jackson Immunoresearch).

Video Microscopy

The inventors used an inverted Leica DMIRBE microscope with an heated and motorized stage combined with a home-made plastic cell chamber to hold the printed glass coverslip, which was covered by a porous membrane allowing $CO_2$ buffering at pH-7.4. Metamorph software (Universal Imaging) was used for image acquisition. Numerous cell divisions were followed using a time-lapse phase contrast on a multi-fields acquisition at a frame rate of one picture every 3 minutes with a 10× magnitude objective. Centrosome movements were followed during mitosis with a 63× apochromat objective lens (Leica) using fluorescent Z acquisitions through a green filter and a phase contrast picture of the cell bottom every 5 minutes.

Video Analysis and Processing

A software has been developed. This software was able to automatically recognise a single fluorescent micropattern within a field and detect the presence of a single cell attached to it. Individual cell divisions were extracted from the 10× phase contrast time-lapse recordings and every picture automatically segmented using a wavelet decomposition and fitted with an ellipse (FIG. 1b). The moment of cell elongation in anaphase was precisely detected, as the shape factor, defined as the ellipse length ratio, suddenly dropped from more than 0.9 to less than 0.6 (FIG. 1c). The angle between the major axis of the ellipse, corresponding to spindle orientation, and the vertical reference of the pattern oriented as shown on FIG. 2 was then recorded. The position of the centre of the round mitotic cell with respect to the pattern was also automatically recorded 6 minutes before anaphase.> Style tag for indented paragraphs within methods section.

Cell Division Axis on Controlled Adhesion

To achieve this goal, the inventors controlled the ability of HeLa cells to adhere and divide on adhesive shapes, using microcontact-printing, a standard micropatterning technique. A range of patterns covering areas from 600 to 900 μm² were designed in which one single cell could spread and divide, but restricted cell movement. Following a double thymidine block, G2 cells were seeded on fibronectin micropatterns and cell division was video-recorded. An automated numerical tool was developed to detect each micropattern in the recorded field and the presence of a single cell attached to it (FIG. 1). Spindle orientation, taken as the orientation of cell elongation at anaphase onset, and the position of the round mitotic cell center were automatically recorded (see Methods). This processing enabled the rapid analysis of a great number of cell divisions.

Fully Adhesive Micropatterns

The efficacy of this approach was confirmed by also observing the correlation between pre-mitotic shape factor and mitotic spindle orientation on micropatterns of similar area. Cells were plated on rectangular (11.5 μm×55 μm=630 μm², outline SF=0.3), discoid (diameter=29 μm, 660 μm², outline SF=1) and right-angled isosceles triangular (edge length=32 μm, 580 μm², outline SF=0.6) adhesive patterns. The majority of cells grown on the rectangular pattern (FIG. 2A) had mitotic spindles aligned along the longest axis, with a total of 69% having an angular deviation of less than 61°. The mitotic spindle orientation of cells plated on discs showed a random distribution (FIG. 2B). With cells grown on the triangular patterns, mitotic spindles were mainly orientated parallel to the longest edge, although the distribution was broader than on the rectangular patterns (FIG. 2C).

The distribution of adhesion sites was determined by examining vinculin-containing structures in pre-mitotic cells. Adhesion sites were mainly found along the periphery of the patterns (FIG. 4a-c), evenly distributed on the border of circular patterns. However, with the rectangular patterns one major site of adhesion was observed at each end of the two longest edges. A significant accumulation of vinculin was also observed at the three vertices of the triangular shapes. Filamentous actin concentration was high along the two long edges of rectangle-shaped cells and the three edges of the triangle-shaped cells, whereas it was evenly distributed along the periphery of the disc-shaped cells.

Mitotic spindle orientation therefore appeared correlated with the global orientation of the vinculin-actin organisation, developed by the interphase G2 cell in response to the adhesion. Spindle orientation was more tightly constrained when the vinculin-actin organisation was unidirectional. In order to discriminate the cellular adhesion profile from the cell outline in this correlation, different adhesion patterns were designed and tested such as the cell outline was not disrupted. These pattern designs attempted to mimic tissue conditions where only restricted portions of the cell membrane are involved in adhesion contacts with neighboring cells.

Peripherally Adhesive Micropatterns

[L] and [bar+dot] micropatterns were designed to provide complementary combinations of adhesive and non-adhesive areas in the same convex envelope as the right-angled isosceles triangle described above (edge length=32 μm, area=580 μm², outline SF=0.6). In every case the mitotic cells were centered on a line that perpendicularly bisects the hypotenuse. On [L] the mitotic cells were tightly clustered near the right angular vertex. Spindles were aligned in a direction parallel to the hypotenuse of the triangle (FIG. 2D). The angular distribution was as restricted as found with the rectangles despite a larger shape factor. Interestingly, the average position of mitotic cells on the [bar+dot] was significantly different from that on [L], being closer to the hypotenuse of the triangle. Strikingly, spindle orientation was also oriented parallel to the hyppotenuse on the [bar+dot] but with a two-fold greater angular distribution (FIG. 2E).

These results demonstrate that, rather than cell shape, it is the distribution of cell adhesions at the cell periphery, which predict mitotic spindle orientation and mitotic cell positioning. Although the triangular distribution of vinculin and filamentous actin in interphase cells was similar and reflected the common cell shape, the [L] and the [bar dot] patterns provided two distinct external boundary conditions that guided the internal assembly of the cell adhesion-actin system. Therefore, actin bundles along non-adhesive sides were consistently thicker and associated with larger vinculin-positive focal adhesions than those along adhesive edges.

The inventors conclude that cells respond to adhesive patterns by unequally distributing the vinculin-actin system, thus replicating the symmetry and weight of the externally imposed adhesive surfaces, a property which is exploited below. They reasoned that these strong actin bundles could bias the intracellular distribution of compartments and other cytoskeleton networks, thus providing guiding cues for cell division and spindle orientation. The mitotic apparatus in cells on [L] would be influenced by a single major unidirectional constraint, whereas those in cells on [bar+dot] would encounter two major perpendicular constraints leading to the same average orientation than on [L] but with a greater variation. Notably, in both cases the resulting constraint lies perpendicular to the only plane of symmetry within both the micropattern and cell; this plane bisects the hypotenuse.

To further analyse the respective roles of spatial distribution and symmetry of adhesives surfaces on guiding the cell response, peripheral patterns with shapes having more than one plane of symmetry were examined. These patterns were based upon a square template and included: a [frame] pattern composed of a hollow square with four axes of symmetry, a [L+dot] pattern, composed of two perpendicular adhesive and two perpendicular non-adhesive edges with only one symmetry plane; and a [twin bars] pattern composed of two pairs of opposite edges, one adhesive the other not, and two axes of symmetry (FIG. 3F-3H). Vinculin-actin structures displayed a behavior as described above; elements along the non-adhesive edges being more conspicuous, thus reflecting within the cell the external symmetries and balances of adhesion surfaces (FIGS. 3F-3H).

On the [frame] pattern (edge length=29 μm, area=900 μm², outline SF=0.4), G2 cells had four equivalent vinculin-actin cables along the edges (FIG. 2F) and mitotic spindles mainly oriented along one or the other diagonal (FIG. 3F). This preferential diagonal orientation, rather than parallel to the edges clearly suggests a process by which spindle sums up the four components of the interphase cytoskeleton to orientate itself. Interestingly, a non-peripheral pattern like [cross], which has the same axes of symmetry as the frame, displayed a similar balance within the vinculin-actin structure (FIG. 3I) and spindle orientation distribution (FIG. 2I). By reducing to one plane of symmetry using the [L+dot], spindles aligned perpendicular to this and the distribution of mitotic cell positions was shifted toward the adhesive bars corner (FIG. 2G).

Interestingly, by having two planes of symmetry using the [twin bars], spindles were mainly oriented along only one axis (FIG. 2H). This axis was parallel to the non adhesive edges, which corresponds to the two strongest vinculin-actin structures (FIG. 3H), and 45° from the long cell axis. Orientation perpendicular to the second plane of symmetry was rare. These results demonstrate that the unbalance within the adhesive distribution is integrated into the process of spindle orientation and can override other geometrical parameters.

In conclusion, the spindle orientation can be directed either by reducing the number of symmetry elements of the adhesive pattern or by biasing their respective weights. The long axis defined by cell outline is not critical and can be experimentally overridden. Cells internally interpret the symmetries and balances of the external adhesive conditions and this appears to guide spindle orientation.

How is the position of the mitotic cell centre controlled by the pattern? Mitotic cell rounding starts with cell retraction (Mitchison, 1992; Cramer and Mitchison. *Mol. Biol. Cell* 8, 109-119, 1997). The inventors observed that cell margins on non-adhesive borders, where actin cables were more abundant, retracted first and the first RFs appeared at the corresponding cell apices. Contact with the adhesive pattern was then progressively retracted, leading the cell body to eventually complete rounding-up close to the adhesive area. This mechanism induced a wide distribution of mitotic cell positions located close to the centre of the [frame], whereas it is much more concentrated on [cross], shifted toward the adhesive corner on [L+dot], and elongated towards the adhesive areas on [twin bars] (see distributions in FIG. 2). Interestingly, whatever the final position of the round cell body, the RFs maintain the connection to the entire pattern (see FIG. 2 right column) and so appeared to influence spindle orientation. This raises the important question of the temporal correlation between spindle formation and cell retraction.

Mitotic Cell Rounding, Centrosome Segregation and Spindle Assembly

The separation of the daughter centrosomes is often taken as the onset of mitosis. But how this event is correlated with cell-rounding is not clearly known. It has been reported for example that centrosome separation often occurs in prometaphase before cell rounding. The inventors reinvestigated this aspect in cells migrating on an infinite adhesive substrate, and in cells immobilized on [L] patterns. As shown on FIG. 4A, the segregation of centrosomes was markedly different in both conditions. With migrating cells, centrosome separation more often preceded cell rounding and the time taken between these events varied between cells. In cells immobilised on [L] the onset of centrosome separation was closely synchronised with cell rounding (FIG. 4B). The centrosomes separated while the nuclear envelope was still present and reached their final positions only after nuclear envelope breakdown (monitored by the redistribution of cytoplasmic centrin-GFP) which happened during cell rounding.

The mechanisms by which the premitotic actin network is remodeled during mitotic cortical retraction and the correlative formation of actin-rich retraction fibers are not fully understood. In order to address whether spindle assembly had to take place during the remodelling of the actin network to be correctly oriented, centrosomes were prevented from separating during cell retraction on [L] patterns by treating premitotic cells with $10^{-7}$ M nocodazole during one hour. This treatment blocked cells in metaphase with unseparated centrosomes but did not block cell rounding. After nocodazole washout, centrosomes separated and formed a bipolar spindle (FIG. 4C). Even if much broader than for the non-treated cells, the distribution of spindle orientations after nocodazole wash-out was still preferentially orientated parallel to the hypotenuse of the triangle (FIG. 4D). This indicates that mitotic cell retraction in the absence of microtubules leads to round cells that are still sensitive to the adhesion pattern. RFs are good candidates for guiding spindle orientation as they are maintained despite nocodazole treatment.

Indeed as with other results of the inventors, the distribution of RFs directly depends upon the adhesion profile. They are almost absent in non-adhesive areas. The respective orientations of their attachments zones on the round cell body systematically correspond to the preferential orientations of spindle poles (FIG. 2). Rectangle, [L] and [twin bars] patterns all provided efficient constraint on spindle orientation and induced the formation of two major opposite cortical attachment zones of RFs. Whereas patterns that induced the formation of more than two major RFs attachment zones on the round cell body ([full triangle], [bar+dot], [frame], [L+dot]) were much less efficient at controlling spindle orientation. For example, despite a similar mitotic cell positioning on the [L] and [L+dot] pattern the additional RFs induced by the dot were sufficient to destabilize spindle orientation. RFs are remarkably straight implying that they are under tension. They therefore appear capable of transmitting the necessary structural and biochemical informations from the premitotic actin-vinculin structure to the spindle apparatus.

Discussion

The inventors have demonstrated that both the position of the mitotic cell and the orientation of the mitotic spindle within the cell are exquisitely sensitive to external adhesion patterns. It is the response of the cell to the adhesive pattern, i-e the co-assembly of adhesion and stress fibers into a non-isotropic network, due to pattern topology, that drives the orientation of the bipolar spindle at the onset of mitosis. It has been shown that the size and orientation of focal adhesions are directly correlated to the traction a cell exerts on the substrate. On fully adhesive square micropatterns, these forces are effectively much stronger at cell vertices where vinculin accumulates. Consequently, the symmetries and unbalances within the vinculin-actin network reflect the directions and intensities of the force distribution at the cell-substrate interface. Indeed, such preferential orientation of the actin cytoskeleton has recently been correlated to a 3d anisotropic force field within adherent cells. The present observations then suggest that the spindle axis is systematically aligned along the force field developed in interphase, which could then be partially maintained during mitosis through the tension of retracting fibers. This alignment creates a stable configuration, proficient for the migration of chromosomes along the traction field, for the formation of daughter cells and for them to recover the cell traction field in order to complete cytokinesis. Indeed, this could be instrumental for maintaining tissue integrity. In conclusion, the present approach has revealed an unexpected link between the global organisation of the cell traction forces and the division axis. Its reproducibility and automatisation should be valuable to reinvestigate signalling involved in spindle interactions with the cell cortex.

Example 2

Materials and Methods
Chemicals
PDMS,: Sylgard, Dow Corning, ref: 1673921, 184 silicone elastomer kit.
Mercapto-silane: Roth Sochiel, ref: SIM6476.0, 3 mercapto-propyulrimethoxy silane.
PEG-mal: Shear Water mPEG-MAL MW: 5000, ref 2D2MOH01.
Fibronectin: Sigma
Trypsin
Microcontact printing µCP
A master template has been made using a photolithographic method developed and fully described by Whitesides et al (Annu. Rev. Biomed. Eng., 2001, p 335-373). Briefly, a silicon wafer coated with a photoresist layer was illuminated with UV through a chrome mask on which the pattern has been designed with an electron beam. An elastomeric poly (dimethylsiloxane), PDMS, stamp was casted on the master and cured 3 hours at 60° C. to reproduce the negative features of the master. The stamp of PDMS was sonicated in ethanol 70% for 2 minutes and dried with blowed air, then oxidized in an air plasma for 10s and inked with the protein solution, 50 µg/mL of fibronectin in water, for 30 minutes. Then the solution was aspirated and the stamp dried with filtered air before being placed in contact with a silanised coverslip for 15 minutes. The coverslip had previously been oxidized with a "piranha" solution (30% $H_2O_2$ 33%, 70% $H_2SO_4$ 96%) for 10 minutes, silanised (in 10 mL methanol, 86 µL acetic acid, 450 µL deionized water, 212 µL mercapto-silane) for 3 h at room temperature, washed in methanol, and dried 10 minutes at 60° C. After removal of the stamp, the printed coverslip was incubated in a maleimide-poly(ethyleneglycol), PEG-mal, solution 10 mg/mL in PBS for 1 hour at room temperature. The coverslip was then gently washed in PBS and ready for cell deposition.

Cell culture and deposition.

Cells were cultured in Dulbecco Modified Eagle Medium with 10% calf serum, 1% penicillin and streptomycine, and 1% glutamine at 37° C. Cells were washed with warmed PBS and removed from their flask with trypsine 2 minutes at 37° C. After removing the trypsine by centrifugation, cells were resuspended in DMEM, with as little serum as possible, and deposited on the printed coverslip at about $10^4$ cells/cm² density. After less than 30 minutes, non-adherent cells were removed. One hour later cells were equilibrated in their constrained shape and ready for fixation or videomicroscopy.

Results

Focal Adhesions and Actin Network

In low serum medium, focal adhesions were strictly restricted to the adhesive pattern. Cell shapes always corresponded to the convex envelope of the adhesive micro-patterns. On the L-shaped micro-patterns, cells had a right-angled triangular shape but did not develop any focal adhesions on the non-adhesive area. Several cell types had shown very specific and repetitive adhesive behaviors on L-shaped micro-patterns. The actin network structure was directly correlated to specific distributions of focal adhesions.

L929

Cells developed focal adhesions all over the adhesive micro-pattern and at the periphery of it, except at the concave sector of the periphery facing the non-adhesive area. Actin fibers were always anchored along both sides of the non adhesive hole and were oriented basically parallel to the hypotenuse of the L-shaped pattern. Distribution of fibronectin followed the L-shaped pattern. (see FIG. 6)

MDCK

Cells developed focal adhesions only at the cell periphery of the adhesive surface, but not at the concave sector of the periphery facing the non-adhesive area. It seems that vinculin accumulated at the cell vertexes (or vertices) and that, if vertexes were close enough, they could make a long continuous adhesive border. Actin fibers are almost restricted to the cell periphery. A similar picture is observed for control cells grown on an infinite adhesive surface, but L-shaped micro-patterns have a strong normalizing effect on the distribution of individual focal adhesions. Distribution of fibronectin followed the L-shaped pattern. (see FIG. 7)

HeLa

Vinculin was abundant in the cytoplasm, distributed in a random manner which suggests the existence of a soluble pool. Cells developed most of their focal complexes at the cell vertexes and along the periphery of the adhesive surface but, once again, not at the concave sector of the periphery facing the non-adhesive area. Actin cable were distributed through the entire cell. Distribution of fibronectin followed the L-shaped pattern. (See FIG. 8)

Microtubule Dynamics

The microtubule network is too dense to show an obvious correlation between its structure and the adhesive pattern. But some proteins associated with the growing plus ends of microtubules, like EB1, can be revealing. Most of the growing ends were localised at the periphery of the right-angled triangular cells, and also close to the nucleating center, the centrosome, from where they seemed to radiate towards cell vertices. (See FIG. 9) EB1 dynamics measured by videorecording confirmed that microtubules were mainly growing towards the two sharp vertices of the right-angle triangular cell. (See FIG. 10)

Centrosome Position

The adhesive patterns allowed the definition of an area with 90% of presence of the projected mean centrioles position in interphase. (See FIG. 11)

Golgi Structure

The microtubule network acts in a very complex way as a scaffold for the Golgi apparatus structure. Cells on adhesive micro-patterns cannot migrate. The whole Golgi structure, which is classically localised at the vicinity of the centrosome, was polarized from CGN to TON not only locally, as observed in classical culture conditions (FIG. 12B), but globally, at the whole organelle level (FIG. 12A). The Golgi apparatus was no longer distorted by cell flattening, but displayed a concentric organization of the various compartments about the centrosome. Also see FIG. 13.

Spindle Orientation

On L-shaped adhesive micro-patterns, more than 80% of the cells divided along an axis which makes an angle with the L hypotenuse smaller than 10°. Even the smallest L-shaped adhesive micro-patterns were efficient to orientate cell division. (See FIG. 14)

As the branches of the L-shaped adhesive micro-patterns became shorter and wider (the non adhesive area decreases) (See FIG. 15), the distribution of the angle between the spindle axis and the hypotenuse got wider. (See FIGS. 16 and 17)

The invention claimed is:

1. A device for adhering at least one cell in a specific and predetermined position with a controlled polarisation of the internal cell organization, comprising:
a plate defining a surface; and,
a plurality of anisotropic adhesive patterns having one or two axis of symmetry on said surface, wherein the size of said patterns is such that only one individual cell can adhere to one of said anisotropic adhesive patterns with a controlled polarisation of the internal cell organization; and the anisotropic adhesive pattern is a concave adhesive pattern that inscribes a surface in which a single cell can bind and said concave adhesive pattern comprises an adhesive area and a non-adhesive area and is an anisotropic adhesive pattern being formed by a single connected adhesive surface or several non-connected adhesive surfaces.

2. The device according to claim 1, wherein said anisotropic adhesive pattern is a concave adhesive pattern that consists of a combination of adhesive elements selected from a line, a curve and a point.

3. The device according to claim 1, wherein said anisotropic adhesive pattern is a concave adhesive pattern.

4. The device according to claim 3, wherein said concave adhesive pattern comprises one or several adhesive lines or curves that form a convex envelope.

5. The device according to claim 4, wherein said convex envelope is a polygon.

6. The device according to claim 5, wherein said polygon is a triangle.

7. The device according to claim 6, wherein said triangle has two adhesive edges.

8. The device according to claim 7, wherein the angle between the two adhesive edges is about 90°.

9. The device according to claim 5, wherein said polygon is a quadrilateral.

10. The device according to claim 9, wherein said quadrilateral has two non-consecutive adhesive edges.

11. The device according to claim 9, wherein said quadrilateral has two consecutive adhesive edges and one adhesive corner.

12. The device according to claim 1, wherein said device comprises at least 100 anisotropic adhesive patterns.

13. The device according to claim 12, wherein said device comprises between 5,000 and 15,000 anisotropic adhesive patterns/cm$^2$.

14. The device according to claim 1 wherein an inscribed surface by the concave adhesive pattern is essentially nonadhesive.

15. A method for immobilizing a cell at a surface, said method comprising:
providing a device according to claim 1;
exposing the plate to at least one cell for a period of time sufficient to allow the cell(s) to bind to the adhesive pattern(s).

16. A method for controlling the cell shape and global internal cell organization, said method comprising:
providing a device according to claim 1;
contacting said plurality of anisotropic adhesive patterns with at least one cell for a period of time sufficient to allow the cell(s) to adhere to the anisotropic adhesive patterns; and,
growing the cell(s) on the anisotropic adhesive patterns while allowing the form of the anisotropic adhesive pattern to influence the shape of the cell and the polarisation of the cell machinery.

17. A method for studying the shape, the global internal cell organization, and/or a function of a cell, said method comprising:
providing a device according to claim 1;
contacting said adhesive pattern(s) with at least one cell for a period of time sufficient to allow the cell(s) to adhere to the anisotropic adhesive patterns;
growing the cell(s) on the anisotropic adhesive pattern(s); and,
observing the shape, the global internal cell organization, the mitosis and/or a function of said cell(s).

18. A method of selecting biologically active compounds, said method comprising:
providing a device according to claim 1;
contacting said anisotropic adhesive patterns with at least one cell for a period of time sufficient to allow the cell(s) to adhere to the anisotropic adhesive patterns;
contacting a test compound with said cell(s);
growing the cell(s) on the anisotropic adhesive patterns; and,
observing the shape, the global internal cell organization, the mitosis, and/or a function of said cell(s).

19. The method according to claim 18, wherein said method comprises an additional step of comparing the shape, the global internal cell organization and/or a function of said cell(s) with cells not contacted by said test compound.

20. The method according to claim 18, wherein the global internal cell organization is evaluated through the position of the centrosome and the position of the Golgi apparatus, the spatial distribution of actin filaments and/or the mitotic spindle orientation.

21. The method according to claim 18, wherein the method comprises an automated analysis of said cell(s) using an image analyser including a specific software using an algorithm designed for such analysis.

22. The method according to claim 21, wherein an automated analysis comprises:
a) identifying the position of anisotropic adhesive patterns on the plate;
b) recording cell images at several times for several identified patterns;
c) fitting an ellipse on the cell outline from cell images; and
d) detecting the division time and determining parameters of interest.

23. A method for determining if a cell has a transformed phenotype associated to a spindle misorientation comprising:
providing a device according to claim 1;
contacting said anisotropic adhesive patterns with cells to test for a period of time sufficient to allow the cells to adhere to the anisotropic adhesive patterns;
growing the cells to test on the anisotropic adhesive patterns;
determining the spindle orientation for each cell and comparing the spindle orientation of different cells;
wherein a spindle orientation dispersion of at least 20° indicates that the tested cell has the transformed phenotype.

24. The device according to claim 1, wherein said device comprises a plurality of anisotropic adhesive patterns isolated from each other by cytophobic regions to which cells do not adhere.

25. The device according to claim 4, wherein the convex envelope contains at least 5% non-adhesive area within said convex envelope.

26. The device according to claim 4, wherein the convex envelope contains at least 10% non-adhesive area within said convex envelope.

27. The device according to claim 4, wherein the convex envelope contains at least 20% non-adhesive area within said convex envelope.

28. The device according to claim 4, wherein the convex envelope contains at least 30% non-adhesive area within said convex envelope.

29. The device according to claim 1, wherein the anisotropic adhesive pattern is a concave adhesive pattern in the form of C, L, U or V.

30. The device according to claim 1, wherein said plate comprises a plurality of discrete anisotropic adhesive patterns arrayed in a predetermined geometric template, said anisotropic adhesive patterns being isolated one from another by cytophobic regions which do not promote adherence of cells, wherein only a single cell can adhere to each discrete anisotropic adhesive pattern and said cytophobic regions are sufficiently wide to prevent cells adhered to said anisotropic adhesive patterns from contacting each other.

31. The device according to claim 30, wherein the cytophobic region is at least 10 μm in width.

32. The device according to claim 1, wherein the anisotropic adhesive pattern is a concave adhesive pattern that inscribes a surface that comprises an adhesive area and a non-adhesive area and at least 75% of said inscribed surface is non-adhesive.

33. The device according to claim 1, wherein the anisotropic adhesive pattern is a concave adhesive pattern that inscribes a surface that comprises an adhesive area and a non-adhesive area and at least 90% of said inscribed surface is non-adhesive.

34. The device according to claim 1, wherein the anisotropic adhesive pattern is a concave adhesive pattern that inscribes a surface that comprises an adhesive area and a non-adhesive area and at least 95% of said inscribed surface is non-adhesive.

35. The device according to claim 1, wherein the anisotropic adhesive pattern is a concave adhesive pattern that inscribes a surface that comprises an adhesive area and a non-adhesive area and at least 99% of said inscribed surface is non-adhesive.

36. The device according to claim 4, wherein the ratio of adhesive are and non-adhesive area in the convex envelope is between 10 and 90%.

37. The device according to claim 4, wherein the ratio of adhesive area and non-adhesive area in the convex envelope is between 20 and 80%.

38. The device according to claim 4, wherein the ratio of adhesive area and non-adhesive area in the convex envelope is between 30 and 70%.

39. The device according to claim 1, wherein the anisotropic adhesive pattern formed by a single connected adhesive surface or several non-connected adhesive surfaces has the form of FIG. 2D, 2E, 2G, 2H, 5A or 5B.

* * * * *

UNITED STATES PATENT AND TRADEMARK OFFICE
CERTIFICATE OF CORRECTION

| | | |
|---|---|---|
| PATENT NO. | : 7,955,838 B2 | Page 1 of 1 |
| APPLICATION NO. | : 10/572101 | |
| DATED | : June 7, 2011 | |
| INVENTOR(S) | : Michel Bornens et al. | |

It is certified that error appears in the above-identified patent and that said Letters Patent is hereby corrected as shown below:

Column 20,
Line 25, "CGN to TON" should read --CGN to TGN--.

Signed and Sealed this
Fourth Day of October, 2011

David J. Kappos
*Director of the United States Patent and Trademark Office*